United States Patent [19]

Rosenberg et al.

[11] Patent Number: 5,063,208
[45] Date of Patent: Nov. 5, 1991

[54] PEPTIDYL AMINODIOL RENIN INHIBITORS

[75] Inventors: Saul H. Rosenberg, Libertyville; Kenneth P. Spina, Chicago; Steven R. Crowley, Vernon Hills, all of Ill.

[73] Assignee: Abbott Laboratories, Abbott Park, Ill.

[21] Appl. No.: 544,072

[22] Filed: Jun. 29, 1990

Related U.S. Application Data

[63] Continuation-in-part of Ser. No. 7,385,836, Jul. 26, 1989, abandoned.

[51] Int. Cl.$^5$ .................. A61K 37/02; C07K 5/08
[52] U.S. Cl. ................................. 514/19; 514/18; 530/331; 530/332; 544/162; 546/141; 546/146; 540/451; 540/476; 540/523; 540/593; 548/225; 548/344; 548/537; 564/153; 564/157
[58] Field of Search ............... 546/280, 279, 141, 146; 548/204, 344, 225, 537; 544/140, 162; 514/19, 18; 530/331, 332; 540/476, 451, 523, 593; 564/153, 157

[56] References Cited

U.S. PATENT DOCUMENTS

| | | |
|---|---|---|
| 4,812,442 | 3/1989 | Boger . |
| 4,837,204 | 6/1989 | Rosenberg et al. . |
| 4,837,204 | 6/1989 | Rosenberg et al. ............ 514/18 |
| 4,845,079 | 7/1989 | Luly et al. . |
| 4,845,079 | 7/1989 | Luly et al. ............ 514/18 |
| 4,906,613 | 3/1990 | Watkins . |
| 4,927,807 | 5/1990 | Stein et al. . |

FOREIGN PATENT DOCUMENTS

| | | |
|---|---|---|
| 0310070 | 4/1989 | European Pat. Off. . |
| 0310071 | 4/1989 | European Pat. Off. . |
| 0310072 | 4/1989 | European Pat. Off. . |
| 0310073 | 4/1989 | European Pat. Off. . |
| 3721855 | 9/1988 | Fed. Rep. of Germany . |
| WO88/05050 | 7/1988 | PCT Int'l Appl. . |
| WO90/00050 | 1/1990 | PCT Int'l Appl. . |

OTHER PUBLICATIONS

Morshima, Biochem. Biophys. Res. Commun. 159 999 (1989).
Hanson, Biochem. Biophys. Res. Commun. 132 155 (1985).
Burger, *Medicinal Chemistry*, 1960, pp. 565–571, 578–581, 600–601.
Dinkewalter et al., *Progress in Drug Research*, 1966, vol. 10, pp. 610–612.
Plattner et al., *J. Med. Chem.* 1988, 31(12), pp. 2277–2288.
Bolis et al., *J. Med. Chem.* 1987, 30(10), pp. 1729–1737.
Haber et al., *J. Cardiovasc. Pharmacol.*, 1987, 10(Supp. 7), pp. S54–S58.

*Primary Examiner*—Lester L. Lee
*Assistant Examiner*—Stephen B. Maebius
*Attorney, Agent, or Firm*—Steven R. Crowley

[57] ABSTRACT

A renin inhibiting compound having an aminodiol functional group is useful for treating hypertension, congestive heart failure and glaucoma and inhibits retroviral protease.

10 Claims, No Drawings

PEPTIDYL AMINODIOL RENIN INHIBITORS

This is a continuation-in-part of U.S. Pat. application Ser. No. 385,836, filed July 26, 1989.

TECHNICAL FIELD

The present invention relates to novel compounds and compositions which inhibit renin, processes for making such compounds, synthetic intermediates employed in these processes and a method of treating hypertension or congestive heart failure with such compounds or in combination with another antihypertensive agent. The present invention also relates to compositions and a method for treating glaucoma with such compounds and a method of inhibiting retroviral proteases with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharamacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavorial and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger, et al. have reported that statine-containing peptides possess potent and specific renin-inhibiting activity (*Nature*, Vol. 303, p. 81, 1983). In addition, Szelke and co-workers have described polypeptide analogs containing a non-peptide link (*Nature*, Vol. 299, p. 555, 1982) which also cause potent renin inhibition and show a high specificity for this enzyme.

DISCLOSURE OF THE INVENTION

In accordance with the present invention, there are compounds of the formula:

$$A\underset{R_1}{\diagdown}\overset{W}{\phantom{x}}\underset{U}{\diagdown}\overset{R_3}{\underset{\phantom{x}}{\diagup}}\underset{\underset{O}{\|}}{\overset{\overset{H}{|}}{N}}\underset{R_4}{\diagdown}\overset{R_8}{\underset{R_5}{\diagup}}D \qquad (I)$$

or a pharmaceutically acceptable salt, ester or prodrug thereof.

A is
(1) heterocyclic,
(2) (heterocyclic)alkyl,
(3) (alkoxy)(alkyl)aminoalkyl,
(4) (alkoxy)aminoalkyl or
(5) substituted carbonyloxy or substituted carbonyloxy analog.

$R_1$ is
(1) loweralkyl,
(2) functionalized alkyl,
(3) aryloxy,
(4) thioaryloxy or
(5) arylamino.

W is
(1) —C(O)—or
(2) —CH(OH)—.

U is
(1) —CH$_2$—or
(2) —N(R$_2$)—wherein
  R$_2$ is
   (i) hydrogen or
   (ii) loweralkyl.

$R_3$ is
(1) loweralkyl,
(2) alkenyl,
(3) alkoxyalkyl,
(4) thioalkoxyalkyl,
(5) ((alkoxy)alkoxy)alkyl,
(6) arylalkyl or
(7) (heterocyclic)alkyl.

$R_4$ is
(1) loweralkyl,
(2) cycloalkylalkyl or
(3) arylalkyl.

$R_5$ is
(1) hydrogen,
(2) loweralkyl,
(3) alkenyl,
(4) formyl or
(5) hydroxyalkyl.

$R_8$ is
(1) —OH or
(2) —NH$_2$.

D is functionalized methylene.

The compounds of formula I contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem. (1976) 45, 13-30.

The term "loweralkyl" as used herein refers to straight or branched chain alkyl radicals containing from 1 to 7 carbon atoms including but not limited to methyl, ethyl, n-propyl, iso-propyl, n-butyl, iso-butyl, sec-butyl, n-pentyl, 2-methylbutyl, 2,2-dimethylpropyl, n-hexyl, 2-methylpentyl, 2,2-dimethylbutyl, n-heptyl, and the like.

The term "alkenyl" as used herein refers to a straight or branched chain radical of 2 to 7 carbon atoms containing a carbon-carbon double bond including, but not limited to, vinyl, propenyl, butenyl and the like.

The term "cycloalkyl" as used herein refers to an alicyclic ring having 3 to 7 carbon atoms.

The term "cycloalkylalkyl" as used herein refers to a cycloalkyl residue appended to a loweralkyl radical and includes but is not limited to cyclohexylmethyl and cyclopentylmethyl.

The term "arylalkyl" as used herein refers to an aryl group appended to a loweralkyl radical including, but not limited to, benzyl, naphthylmethyl and the like.

The term "(heterocyclic)alkyl" as used herein refers to a heterocyclic ring (as defined below) appended to a loweralkyl radical, including, but not limited to imidazolylmethyl, thiazolylmethyl and the like.

The term "(4-membered heterocyclic)alkyl" as used herein refers to a 4-membered heterocyclic group appended to a loweralkyl radical.

The term "hydroxyalkyl" as used herein refers to —OH appended to a loweralkyl radical.

The term "alkoxyalkyl" as used herein refers to an alkoxy group appended to a loweralkyl radical.

The term "thioalkoxyalkyl" as used herein refers to a thioalkoxy group appended to a loweralkyl radical.

The term "((alkoxy)alkoxy)alkyl" as used herein refers to an alkoxy group appended to an alkoxy group which is appended to a loweralkyl radical including, but not limited to, methoxymethoxymethyl and the like.

The term "polyalkoxyalkyl" as used herein refers to a polyalkoxy residue appended to a loweralkyl radical including, but not limited to, methoxyethoxymethoxymethyl and the like.

The term "aminoalkyl" as used herein refers to —$NH_2$ appended to a loweralkyl radical.

The term "alkylaminoalkyl" as used herein refers to —$NHR_{25}$ appended to a loweralkyl radical, wherein $R_{25}$ is a loweralkyl radical.

The term "dialkylaminoalkyl" as used herein refers to a dialkylamino group appended to a loweralkyl radical.

The term "(N-protected)aminoalkyl" as used herein refers to —$NHR_{26}$ appended to a loweralkyl group, wherein $R_{26}$ is an N-protecting group.

The term "(N-protected)(alkyl)aminoalkyl" as used herein refers to —$NR_{26}R_{27}$, which is appended to a loweralkyl radical, wherein $R_{26}$ is defined as above and $R_{27}$ is a loweralkyl group.

The term "(heterocyclic)aminoalkyl" as used herein refers to a (heterocyclic)amino group appended to a loweralkyl radical.

The term "(heterocyclic)(alkyl)aminoalkyl" as used herein refers to a (heterocyclic)(alkyl)amino group appended to a loweralkyl radical.

The term "((heterocyclic)alkyl)aminoalkyl" as used herein refers to a ((heterocyclic)alkyl)amino group appended to a loweralkyl radical.

The term "((heterocyclic)alkyl)(alkyl)aminoalkyl" as used herein refers to a ((heterocyclic)alkyl)(alkyl)amino group appended to a loweralkyl radical, The term "aryloxyalkyl" as used herein refers to an aryloxy group appended to a loweralkyl radical.

The term "thioaryloxyalkyl" as used herein refers to a thioaryloxy group appended to a loweralkyl radical.

The term "arylaminoalkyl" as used herein refers to an arylamino group appended to a loweralkyl radical.

The term "alkylsulfonylalkyl" as used herein refers to $R_{28}S(O)_2$—, wherein $R_{28}$ is a loweralkyl group, appended to a loweralkyl radical.

The term "arylsulfonylalkyl" as used herein refers to $R_{29}S(O)_2$—, wherein $R_{29}$ is an aryl group, appended to a loweralkyl radical.

The term "carboxyalkyl" as used herein refers to a carboxylic acid group (—COOH) appended to a loweralkyl radical.

The term "(alkoxy)aminoalkyl" as used herein refers to an alkoxy group appended to an amino group which in turn is appended to a loweralkyl radical.

The term "(alkoxy)(alkyl)aminoalkyl" as used herein refers to an —$NR_{30}R_{31}$ group appended to a loweralkyl radical wherein R is an alkoxy group and $R_{31}$ is a loweralkyl group.

The term "haloalkyl" as used herein refers to a loweralkyl radical in which one or more hydrogen atoms are replaced by halogen including, but not limited to, fluoromethyl, 2-chloroethyl, trifluoromethyl, 2,2-dichloroethyl and the like.

The term "azidoalkyl" as used herein refers to a —$N_3$ group appended to a loweralkyl radical.

The term "functionalized alkyl" as used herein includes cycloalkylalkyl, arylalkyl, (heterocyclic)alkyl, aryloxyalkyl, thioaryloxyalkyl, arylaminoalkyl and the like.

The term "alkylene" as used herein refers to a straight or branched chain spacer radical containing 1 to 7 carbon atoms including, but not limited to, —$CH_2\geq$, —$CH(CH_3)$—, —$(CH_2)_3$—, —$CH_2CH_2CH(CH_3)$— and the like.

The term "functionalized methylene" as used herein includes —$C(R_6)(R_7)(R_9)$ wherein
$R_6$ is
(1) hydrogen,
(2) loweralkyl,
(3) alkenyl,
(4) arylalkyl,
(5) hydroxyalkyl,
(6) alkoxyalkyl,
(7) azidoalkyl,
(8) carboxyalkyl,
(9) thioalkoxyalkyl,
(10) alkylsulfonylalkyl,
(11) arylsulfonylalkyl,
(12) aryloxyalkyl,
(13) thioaryloxyalkyl or
(14) haloalkyl,
$R_7$ is
(1) hydrogen or
(2) loweralkyl and
$R_9$ is (1) —OH or
(2) —NH$_2$.

The term "alkylamino" as used herein refers to —NHR$_{32}$ wherein R$_{32}$ is a loweralkyl group.

The term "dialkylamino" as used herein refers to —NR$_{33}$R$_{34}$ wherein R$_{33}$ and R$_{34}$ are independently selected from loweralkyl.

The term "arylamino" as used herein refers to —NHR$_{35}$ wherein R$_{35}$ is an aryl group.

The term "(heterocyclic)amino" as used herein refers to —NHR$_{36}$ wherein R$_{36}$ is a heterocyclic group.

The term "((heterocyclic)alkyl)(alkyl)amino" as used herein refers to —NR$_{37}$R$_{38}$ wherein R$_{37}$ is a heterocyclic alkyl group and R$_{38}$ is a loweralkyl group.

The term "((heterocyclic)alkyl)amino" as used herein refers to —NHR$_{39}$ wherein R$_{39}$ is a heterocyclic alkyl group.

The term "(heterocyclic)(alkyl)amino" as used herein refers to —NR$_{40}$R$_{41}$ wherein R$_{40}$ is a heterocyclic group and R$_{41}$ is a loweralkyl group.

The terms "alkoxy" and "thioalkoxy" as used herein refer to R$_{42}$O— and R$_{42}$S—, respectively, wherein R$_{42}$ is a loweralkyl group.

The term "aryloxy" as used herein refers to —OR$_{43}$ wherein R$_{43}$ is an aryl group.

The term "thioaryloxy" as used herein refers to —SR$_{44}$ wherein R$_{44}$ is an aryl group.

The term "polyalkoxy" as used herein refers to R$_{45}$O—, wherein R$_{45}$ is a straight or branched chain containing 1-5, C$_n$—O—C$_{n'}$ linkages wherein n and n' are independently 1-3.

The term "substituted carbonyloxy or substituted carbonyloxy analog" as used herein includes R$_{13}$—Q—B— wherein B is
(i) —NH—,
(ii) —N(loweralkyl)—,
(iii) —S—,
(iv) —O—,
(v) —CH$_2$— or
(vi) —CH(OH)—, Q is
(i) —C(O)—,
(ii) —S(O)—,
(iii) —S(O)$_2$— or
(iv) —CH(OR$_{60}$)— wherein R$_{60}$ is hydrogen, loweralkyl or —C(O)R$_{61}$ wherein R$_{61}$ is loweralkyl and R$_{13}$ is
(i) a 4-membered heterocycle,
(ii) (4-membered heterocyclic)alkyl,
(iii) heterocyclic substituted by haloalkyl or cycloalkyl,
(iv) (heterocyclic)alkyl substituted by haloalkyl or cycloalkyl,
(v) (heterocyclic)amino,
(vi) (heterocyclic)aminoalkyl,
(vii) (heterocyclic)(alkyl)amino,
(viii) (heterocyclic)(alkyl)aminoalkyl,
(ix) ((heterocyclic)alkyl)amino,
(x) ((heterocyclic)alkyl)aminoalkyl,
(xi) ((heterocyclic)alkyl)(alkyl)amino,
(xii) ((heterocyclic)alkyl)(alkyl)aminoalkyl or
(xiii) R$_{14}$—G—R$_{15}$— wherein R$_{14}$ is loweralkyl or aryl, R$_{15}$ is alkylene, and G is —S—, —S(O)—, —S(O)$_2$—, —O—, —NH— or —N(loweralkyl)—.

The term "halo" as used herein refers to Cl, Br, F or I substituents.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "heterocyclic group" or "heterocyclic" as used herein refers to any 3- or 4-membered ring containing a heteroatom selected from oxygen, nitrogen and sulfur, or a 5- or 6-membered ring containing one, two or three nitrogen atoms; one nitrogen and one sulfur atom; or one nitrogen and one oxygen atom; wherein the 5-membered ring has 0-2 double bonds and the 6-membered ring has 0-3 double bonds; wherein the nitrogen and sulfur heteroatoms may optionally be oxidized; wherein the nitrogen heteroatom may optionally be quaternized; and including any bicyclic group in which any of the above heterocyclic rings is fused to a benzene ring or another 5- or 6-membered heterocyclic ring independently as defined above. Heterocyclics in which nitrogen is the heteroatom are preferred. Fully saturated heterocyclics are also preferred. Preferred heterocyclics include: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, N-methyl piperazinyl, azetidinyl, N-methyl azetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substitutents independently selected from hydroxy, halo, oxo (=O), alkylimino (R*N= wherein R* is a loweralkyl group), amino, alkylamino, dialkylamino, alkoxy, polyalkoxy, loweralkyl, cycloalkyl or haloalkyl.

The most preferred heterocyclics include imidazolyl, pyridyl, piperazinyl, N-methyl piperazinyl, azetidinyl, N-methyl azetidinyl, thiazolyl, thienyl, triazolyl and the following:

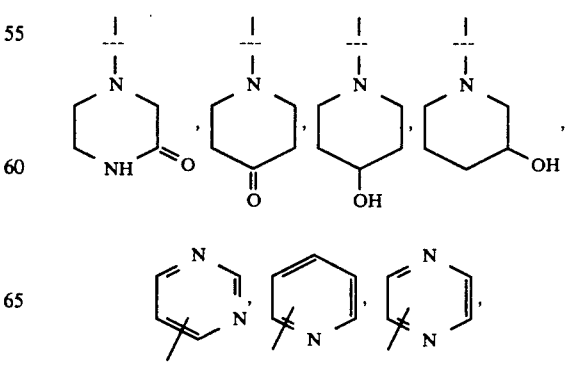

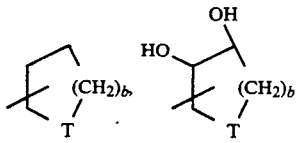

wherein b is 1 or 2 and T is N, NH, O, S, provided that T is the point of connection only when T is N,

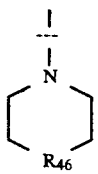

wherein R₄₆ is NH, N-loweralkyl, O, S, or SO₂, or

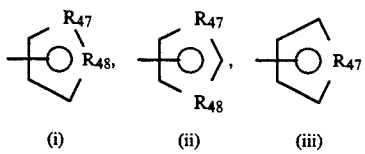

wherein the symbols (i), (ii) and (iii) represent 5-membered heterocycles containing one or more heteroatoms and containing 2 double bonds; wherein $R_{47}$ is N, O, or S and not the point of connection and $R_{48}$ is N when it is the point of connection or NH, O or S when it is not the point of connection.

The term "N-protecting group" or "N-protected" as used herein refers to those groups intended to protect the N-terminus of an amino acid or peptide or to protect an amino group against undesirable reactions during synthetic procedures or to prevent the attack of exopeptidases on the compounds or to increase the solubility of the compounds and includes but is not limited to sulfonyl, acyl, acetyl, pivaloyl, t-butyloxycarbonyl (Boc), carbonylbenzyloxy (Cbz), benzoyl or an L- or D-aminoacyl residue, which may itself be N-protected similarly.

The term "0-protecting group" as used herein refers to a substitutent which protects hydroxyl groups against undesirable reactions during synthetic procedures and includes but is not limited to substituted methyl ethers, for example methoxymethyl, benzyloxymethyl, 2-methoxyethoxymethyl, 2-(trimethylsilyl)ethoxymethyl, benzyl and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methyl acetal, acetonide and benzylidene acetal; cyclic ortho esters, for example, methoxymethylene; cyclic carbonates; and cyclic boronates.

The terms "Ala", "Nle" and "Met" as used herein refer to alanine, norleucine and methionine respectively. In general, the amino acid abbreviations used herein follow the IUPAC-IUB Joint Commission on Biochemical Nomenclature for amino acids and peptides (Eur. J. Biochem. 1984, 158, 9-31).

The compounds of the invention can be made as shown in Schemes 1–2. Intermediates (1) and (2) can be prepared according to methods described in U.S. Pat. No. 4,845,079, issued July 4, 1989, and U.S. Pat. No. 4,837,204, issued June 6, 1989, which are hereby incorporated by reference. In the schemes, A, $R_1$, $R_2$, $R_3$, $R_4$, $R_5$, $R_8$, W, U and D are as defined above.

In particular, the process shown in Scheme 1 discloses the coupling of an N-functionalized amino acid (1) with an amine (2) to provide (3). The coupling reaction is accomplished using the diimide method which employs N-ethyl-N'-(3-dimethylaminopropyl) carbodiimide, 1-hydroxybenzotriazole, and N-methylmorpholine.

Alternatively, Scheme 2 discloses the coupling of N-protected amino acid (4) ($P_1$ is an N-protecting group) with amine (2). Deprotection provides amine (5) which is coupled with carboxylic acid (6) to provide (3).

Other methods known in the art can be used to accomplish the amide bond forming coupling reactions. In particular, activated derivatives of the carboxylic acids can be used in the coupling reactions. Such activated derivatives include acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

Scheme 1

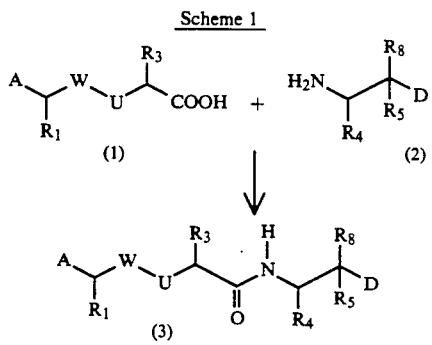

Scheme 2

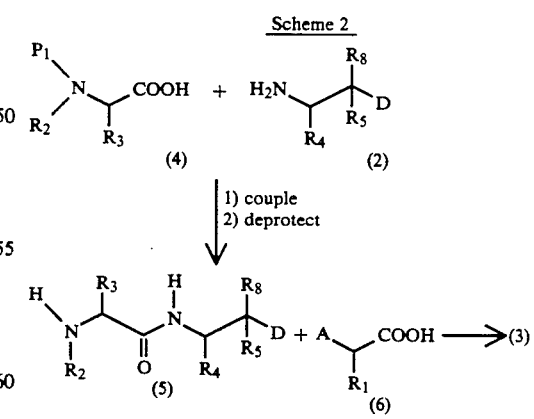

Other intermediates useful for the preparation of the compounds of formula I and methods for their preparation are disclosed in U.S. Pat. No. 4,837,204, issued June 6, 1989, which is hereby incorporated by reference and U.S. Pat. No. 4,845,079, issued July 4, 1989, which is hereby incorporated by reference.

The following Examples will serve to further illustrate preparation of the novel compounds of the invention.

EXAMPLE 1

(2S,3R,4S)-2-Amino-1-cyclohexyl-3,4-dihydroxy-6-methylheptane (2S,3R,4S)-2-[(tert-Butyloxycarbonyl)amino]-1-cyclohexyl-3,4-dihydroxy-6-methylheptane (10.00 g, 29.11 mmol, Luly et al., *J. Org. Chem.* 1988, 53, 6109) was stirred for 1 h in 4M HCl/dioxane. The solvent was evaporated and the residue was dissolved in water which was washed with ether and then made basic with solid $K_2CO_3$. The mixture was saturated with solid NaCl and extracted into chloroform which was dried over $Na_2SO_4$ and evaporated to afford 7.09 g (100%) of a white solid, m.p. 110°–111° C.

EXAMPLE 2

Boc-L-(1-Pyrazolyl)alanine.

Pyrazole (700 mg, 10.3 mmol) and N-(tert-butyloxycarbonyl)-L-serine-β-lactone (1.707 g, 9.117 mmol, Arnold et al., *J. Am. Chem. Soc.* 1985, 107, 7105) in $CH_3CN$ (75 ml) were heated at 52° C. for 72 h. The solvent was evaporated and the residue was dissolved in hot methanol (8 ml) and then water (24 ml) was added with heating until the mixture became turbid. The mixture was cooled to room temperature with rapid stirring, and after stirring overnight 745 mg (32%) of the desired product was collected as a white solid. TLC (20% methanol/1% acetic acid/79% chloroform) $R_f=0.38$; $^1$H NMR (CDCl$_3$) δ7.65 (d,1H), 7.41 (d,1H), 6.30 (dd,1H), 5.48 (br,1H), 4.82 (dd, 1H), 4.67 (dd,1H), 4.48 (m,1H), 1.47 (s,9H), m.p. 130°–134° C.

EXAMPLE 3

N-Boc-3-(4-thiazolyl)-L-alanine

EXAMPLE 3A

Diethyl (2-Bromoallyl)acetamidomalonate

To a stirred mixture of diethyl acetaminomalonate (217 g, 1.0 mol) and 2,3-dibromopropene (240 g, 1.2 mol) in dry tetrahydrofuran (2.50 L), under nitrogen, was added sodium hydride (26.4 g, 1.1 mol) in several portions. The reaction mixture was stirred at room temperature for 30 min, then heated to reflux. After heating for 18 h, the resultant slurry was cooled to room temperature and suction filtered through a short pad of silica gel. The solid residue was washed with tetrahydrofuran (2×50 mL), and the filtrates were combined and concentrated. The residue was dissolved in ethyl acetate (2.0 L), washed with water and brine, and then was dried over MgSO$_4$. Filtration and concentration gave a yellow oil which solidified upon drying. The resultant solid was recrystallized from a mixture of hot ethyl acetate/hexane to give 301 g (89%) of the desired product: m.p. 85°–87° C.

EXAMPLE 3B

Diethyl (3-Bromo-2-oxo-propyl)acetamidomalonate

To a cold (0° C.), stirred solution of the resultant compound from Example 3A (280 g, 0.83 mol) in a mixture of 2:1 acetonitrile/water (1.68 L) was added solid N-bromosuccinimide (193 g, 1.08 mol) in three portions over a period of 15 min. The resultant orange mixture was stirred at 0° C. for an additional period of 1 h and then was allowed to warm to room temperature. After 4 h, the reaction mixture was treated with 10% aqueous sodium thiosulfate, diluted with ethyl acetate, and washed sequentially with water, 10% aqueous NaHSO$_4$ (3 X), water, and brine. Drying (MgSO$_4$) and concentration afforded a yellow solid which was recrystallized from a mixture of ethyl acetate and hexane to give 247 g (85%) of the desired compound as a white solid: m.p. 97°–98.5° C.

EXAMPLE 3C

Diethyl (4-Thiazolylmethyl)acetamidomalonate

A 5 L, 3-neck round bottom flask equipped with a mechanical stirrer, stopper and a drying tube was charged with the resultant compound from Example 3B (325 g, 0.92 mol) and flushed with nitrogen. A freshly prepared solution of thioformamide in tetrahydrofuran (0.8M, 1.25 L) was added in one portion. The reaction mixture was stirred at room temperature for 4 h. The resultant slurry was then diluted with ether (1.25 L) and cooled to 0° C. The solid was then collected by suction filtration and washed with cold ether (3×) to give the title compound as the hydrochloride salt. This material was transferred to a 4 L separatory funnel, slurried with ethyl acetate (2 L) and basified by the careful addition of 2M NaOH. The organic layer was separated, washed with water and brine, and then dried over MgSO$_4$. Filtration and concentration afforded a pale yellow oil which solidified upon drying to give 242 g of the desired compound. This material was recrystallized from an ethyl acetate/hexane mixture to afford 185.6 g (64%) of pure material: m.p. 104°–106° C.

EXAMPLE 3D

N-Acetyl-3-(4-thiazolyl)-DL-alanine Ethyl Ester

To a stirred solution of the resultant compound from Example 3C (185.6 g, 0.59 mol) in a mixture of tetrahydrofuran (620 mL) and ethanol (310 mL) was added aqueous 2M LiOH (325 mL, 0.65 mol) dropwise over 20 min. After stirring at room temperature for 2.5 h, the reaction mixture was concentrated and the resultant aqueous mixture was extracted with ether (3×200 mL), adjusted to pH 3 with 3M HCl, and concentrated under reduced pressure. Residual water was removed by evaporating portions of toluene (2×200 mL). The residue was diluted with toluene (1.5 L) and the resultant slurry was heated to reflux with separation of water (Dean-Stark trap). After 3 h the reaction mixture was cooled to room temperature, diluted with ethyl acetate (1.5 L) and suction filtered through SiO$_2$ (60 g). The solids were washed with additional ethyl acetate (4×500 mL) and the combined organics were concentrated to afford a pale yellow oil which solidified on drying (0.5 torr) to afford 119.6 g (84%) of the desired compound: m.p. 58°–62° C.

EXAMPLE 3E

N-Acetyl-3-(4-thiazolyl)-L-alanine and N-Acetyl-3-(4-thiazolyl)-D-alanine Ethyl Ester A 5 L, 3-neck round bottom flask equipped with a mechanical stirrer was charged with the resultant compound from Example 3D (210 g, 0.87 mol), distilled water (1.6 L), and 1M aqueous KCl (0.8 L). The homogeneous solution was adjusted to pH 7.0 with 0.1M NaOH and then was treated with Subtilisin Carlsberg (1.8 g) dissolved in 0.1 M aqueous KCl (25 mL). The reaction mixture was stirred at room temperature with 1.0M NaOH added as required to maintain the pH at 6.25-7.25. After 4 h, 430 mL of base had been consumed and the reaction was judged to be complete. The reaction mixture was then extracted with chloroform (4×1.5 L), the aqueous phase was carefully acidified to pH 4 with 2M HCL and then was concentrated under reduced pressure. Residual water was removed by consecutive evaporation of portions of toluene (3×500 mL) and ethanol (3×500 mL). The residue was taken up in warm ethanol and suction filtered to remove inorganic salts. The solids were washed with warm ethanol (3×400 mL) and the filtrates were concentrated to afford 92.6 g (50%) of N-acetyl-3-(4-thiazolyl)-L-alanine as a white solid: m.p. 186 °C.

The combined chloroform fractions from the extractions were washed with saturated aqueous NaHCO$_3$, water, and brine and then were dried over MgSO$_4$Filtration and concentration gave 103 g (49%) of N-acetyl-3-(4-thiazolyl)-D-alanine ethyl ester. This material could be further purified by recrystallization from ethyl acetate/hexane: m.p. 79°-80.5 °C.

EXAMPLE 3F

Epimerization of N-Acetyl-3-(4-thiazolyl)-D-alanine Ethyl Ester

A 2 L round bottom flask equipped with a magnetic stirrer, reflux condenser, and nitrogen inlet was charged with sodium (0.96 g, 0.045 mol) and ethanol (900 mL) and the mixture was allowed to reflux until the sodium was consumed. The resultant solution of sodium ethoxide was cooled slightly, and N-acetyl-3-(4-thiazolyl)-D-alanine ethyl ester from Example 3E (102 g, 0.42 mol) was added. The reaction mixture was then heated to reflux. After 3 h the solution was cooled to room temperature, quenched with glacial acetic acid (0.045 mol) and concentrated to remove ethanol. The residue was diluted with ethyl acetate, washed with water and brine and dried over MgSO$_4$. Filtration and concentration gave a yellow oil which was purified by recrystallizing from a mixture of hot ethyl acetate and hexane to yield 89 g (87%) of material identical to that obtained from Example 11.

EXAMPLE 3G 3-(4-Thiazolyl)-L-alanine Dihydrochloride

A 2 L round bottom flask equipped with a magnetic stirrer was charged with N-acetyl-3-(4-thialzoyl)-L-alanine alanine from Example 3E (92.6 g, 0.43 mol) and 6M HCl (1 L). The resultant solution was heated to reflux. After 3 h the mixture was allowed to cool to room temperature. The solution was then concentrated under reduced pressure, evaporated from toluene (3×200 mL), and dried under vacuum overnight to give 120 g of a slightly wet solid. This material was used in the next reaction without further purification.

EXAMPLE 3H

N-Boc-3-(4-thiazolyl)-L-alanine

A 4 L Erlenmeyer flask equipped with a mechanical stirrer was charged with the resultant compound from Example 3G (125.9 g) and tetrahydrofuran (1.5 L) and the mixture was adjusted to pH 6.6 with sodium bicarbonate. The resultant solution was then adjusted to pH 8.9 with 3.0M NaOH and a solution of di-tert-butyldicarbonate (117.8 g, 0.51 mol) in tetrahydrofuran (150 mL) was added. The reaction mixture was vigorously stirred at room temperature for 40 h. The tetrahydrofuran was removed under vacuum, the pH of the residue was adjusted to 2.0 with 3.0M HCl and the mixture was extracted with ethyl acetate (3×300 mL). The combined extracts were dried over MgSO$_4$, filtered, and concentrated to give 150 g of a white solid. Recrystallization from hot 1:1 ethyl acetate/hexane (1.06 L) gave 107.6 g (82 % from the resultant compound of Example 12) of the desired compound: m.p. 115 °C.; [α]D = +129.8 (c=1.04, CHCl$_3$).

Anal. (C$_{11}$H$_{16}$N$_2$O$_2$).
Calcd: C, 48.53; H, 5.88; N, 10.29.
Found: C, 48.58; H, 5.91; N, 10.17.

EXAMPLE 4

Boc-L-(1-Imidazolyl)alanine Methyl Ester.

Imidazole (250 mg, 3.67 mmol) and N-(tert-butyloxycarbonyl)-L-serine-β-lactone (350.0 mg, 1.87 mmol, Arnold et al., *J. Am. Chem. Soc.* 1985, 107, 7105) in CH$_3$CN (9 ml) were stirred at room temperature for 24 h. The mixture was cooled to 0° C., treated with diazomethane in ether, evaporated, and chromatographed on silica gel with 3% methanol in chloroform to afford 305 mg (61%) of the desired product as an oil. 1H NMR (CDCl$_3$) δ7.39 (s,1H), 7.05 (s,1H), 6.82 (s,1H), 5.18 (br,1H), 4.58 (m,1H), 4.42 (m,2H), 3.79 (s,3H), 1.47 (s,9H).

EXAMPLE 5

Boc-L-(1-Imidazolyl)alanine.

The resultant compound from Example 173 (301.0 mg, 1.12 mmol) in dioxane (6 ml) at 0° C. was treated with LiOH.H$_2$O (64.0 mg, 1.53 mmol) in water (4 ml). After 1 h the reaction was quenched with 2.0M HCl (0.75 ml, 1.50 mmol) and evaporated to a white foam which was used without further purification.

EXAMPLE 6

Boc-L-(2-Thienyl)alanine

To L-(2-thienyl)alanine-OH (0.974 g, 5.69 mmol) in water (4 mL) and dioxane (4 mL) was added triethylamine (1.20 mL, 8.56 mmol) and 2-(tert-butoxycarbonyloxyimino)-2-phenylacetonitrile (1.54 g, 6.25 mmol). After 60 h the mixture was diluted with water (10 mL), washed with ether, cooled to 0° C., acidified to pH2 with 2M HCl and extracted into chloroform which was dried over Na$_2$SO$_4$ and evaporated to afford 1.50 g (97%) of an oil. 1H NMR (CDCl$_3$) δ7.19 (1H,dd), 6.96 (1H,dd), 6.86 (1H,dd), 5.09 (1H,br d), 4.50-4.70 (2H,m), 3.30-3.50 (2H,m), 1.46 (9H,s).

EXAMPLE 7

H-L-(4-Thiazolyl)Ala Amide of (2S,3R,4S)-2-Amino-1-cyclohexyl-3,4-dihydroxy-6-methylheptane

EXAMPLE 7A

Boc-L-(4-Thiazolyl)Ala Amide of (2S,3R,4S)-2-Amino-1-cyclohexyl-3,4-dihydroxy-6-methylheptane (2S,3R,4S)-2-[(tert-Butyloxycarbonyl)amino]-1-cyclohexyl-3,4-dihydroxy-6-methylheptane (5.05 g, 14.7 mmol, Luly et al., J. Org. Chem. 1988, 53, 6109) was stirred for 90 min in 4M HCl in ethanol and then evaporated. Ether was added and evaporated 3 times and the residue was dried under high vacuum. To this residue was added 1-hydroxybenzotriazole (5.57 g, 41.2 mmol), the resultant acid from Example 3H (4.00 g, 14.7 mmol), dimethylformamide (60 mL) and N-methylmorpholine (3.40 mL, 30.9 mmol). The mixture was cooled to −23° C., treated with 1-(3-dimethylaminopropyl)-3-ethylcarbodiimide hydrochloride (4.03 g, 21.0 mmol). After 2 h at −23° C. and 21 h at ambient temperature the mixture was poured into saturated $NaHCO_3$ solution and extracted into ethyl acetate. The organic layer was washed with water and brine, then dried over $Na_2SO_4$ and evaporated to a white solid which was recrystallized from 1:15 (v/v) methylene chloride/ether (multiple crops) affording 6.28 g (86%) of the desired product as a flaky white solid: m.p. 159°–160 ° C.; TLC (15% $CH_3OH$/85% $CHCl_3$) $R_f$=0.63; $^1H$ NMR ($CDCl_3$) δ8.78 (1H, d), 7.14 (1H, d), 6.18 (2H, br d), 4.44 (1H, dd), 4.27 (1H, m), 4.10 (1H, m), 3.37 (1H, dd), 3.30–3.12 (3H, m), 1.89 (1H, septet), 1.46 (9H, s), 0.94 (3H, d), 0.88 (3H, d).

Anal. ($C_{25}H_{43}N_3O_5S$).
Calcd: C, 60.33; H, 8.71; N, 8.44.
Found: C, 60.43; H, 8.68; N, 8.51.

EXAMPLE 7B

H-L-(4-Thiazolyl)Ala Amide of (2S,3R,4S)-2-Amino-1-cyclohexyl-3,4-dihydroxy-6-methylheptane Trifluoroacetic acid (50 mL) was slowly added via cannula to a solution of the resultant compound from Example 7A (6.27 g, 12.6 mmol) in methylene chloride (50 mL) at 0° C. The reaction was stirred 3 h at 0° C. and concentrated in vacuo (40° C. bath) to an oil which was basified to pH 10–11 with aqueous $K_2CO_3$. The product was extracted into chloroform, dried over $Na_2SO_4$, filtered, and concentrated to a foam. Recrystallization from 1:4 (v/v) methylene chloride/hexane gave 5.00 g (100%) of the desired product as a fluffy white solid: m.p. 111°–112° C.; TLC (15% $CH_3OH$/85% $CHCl_3$) $R_f$=0.46; $^1H$ NMR ($CDCl_3$) δ8.77 (1H, d), 7.40 (1H, br d), 7.13 (1H, d), 4.54 (1H, m), 4.25 (1H, m), 3.80 (1H, dd), 3.33 (1H, dd), 3.25–3.12 (3H, m), 0.95 (3H, d), 0.86 (3H, d).

Anal ($C_{20}H_{35}N_3O_3S$)
Calcd: C, 60.42; H, 8.87; N, 10.57.
Found: C, 60.05; H, 8.65; N, 10.42.

EXAMPLE 8

Boc-L-(1-Pyrazolyl)Ala Amide of (2S,3R,4S)-2-Amino-1-cyclohexyl-3,4-dihydroxy-6-methylheptane To the resultant compound from Example 1 (778.0 mg, 3.20 mmol), the resultant compound from Example 2 (742.0 mg, 2.91 mmol), 1-hydroxybenzotriazole (1.060 g, 7.84 mmol) and N-methylmorpholine (0.38 mL, 3.46 mmol) in dimethylformamide (15 mL) at −23° C. was added 1-(3-dimethylaminopropyl)-3-ethylcarbodiimide hydrochloride (796.0 mg, 4.15 mmol). After 2 h at −23° C. and 14 h at ambient temperature the mixture was poured into saturated $NaHCO_3$ solution which was extracted twice with ethyl acetate. The combined organic phases were washed with water and brine, dried over $Na_2SO_4$ and evaporated to a residue which was chromatographed on silica gel with 1.5% methanol in chloroform to afford 1.372 g (98%) of a white solid, m.p. 161°–163° C.; TLC (10% $CH_3OH$/90% $CHCl_3$) $R_f$=0.59.

Anal ($C_{25}H_{44}N_4O_5$)
Calcd: C, 62.47; H, 9.23; N, 11.66.

Found: C, 62.45, H, 9.21, N, 11.66.

EXAMPLE 9

Boc-L-(1-Imidazolyl)Ala Amide of (2S,3R,4S)-2-Amino-1-cyclohexyl-3,4-dihydroxyl-6-methylheptane Using the procedure of Example 8 with the resultant acid from Example 5 and chromatographing the final product on silica gel with 3% methanol in chloroform gave the desired product as a white solid, m.p. 123°–127° C. TLC (10% $CH_3OH$/90% $CHCl_3$) $R_f$=0.31.

EXAMPLE 10

Boc-L-(2-Thienyl)Ala Amide of (2S,3R,4S)-2-Amino-1-cyclohexyl-3,4-dihydroxy-6-methylheptane Using the procedure of Example 8 with the resultant acid from Example 6 gave the desired product. TLC (50% ethyl acetate/50% hexane) $R_f$=0.55; $^1H$ NMR ($CDCl_3$) δ7.22 (1H,dd), 6.97 (1H,dd), 6.90 (1H,dd), 6.00 (1H,d), 4.98 H, br), 1.45 (9H,s), 0.95 (3H,d), 0.90 (3H,d).

EXAMPLE 11

Boc-Nle Amide of (2S,3R,4S)-2-Amino-1-cyclohexyl-3,4-dihydroxy-6-methylheptane

Using the procedure of Example 8 and replacing the resultant acid from Example 2 with Boc-L-nor-Leucine (Boc-Nle-OH), gave, after recrystallization from methylene chloride/hexane, the desired product. TLC (ethyl acetate) $R_f$=0.64; $^1H$ NMR ($CDCl_3$) δ6.20 (1H,d), 4.88 (1H,br), 4.33 (1H,ddd), 4.02 (1H,dd), 3.25–3.35 (1H,m), 3.20 (1H,dd), 1.46 (9H,s).

EXAMPLE 12

Boc-Met Amide of (2S,3R,4S)-2-Amino-1-cyclohexyl-3,4-dihydroxy-6-methylheptane

Using the procedure of Example 8 and replacing the resultant acid from Example 2 with Boc-Met-OH gave the desired product.

EXAMPLE 13

H-L-(1-Pyrazolyl)Ala Amide of (2S,3R,4S)-2-Amino-1-cyclohexyl-3,4-dihydroxy-6-methylheptane To the resultant compound from Example 8 (1.73 g) in methylene chloride (30 mL) at 0° C. was added trifluoroacetic acid (30 mL) over 30 min. After 3 h at 0° C. the solvent was evaporated (40° C. bath). The mixture was dissolved in water, made basic with solid $K_2CO_3$, saturated with solid NaCl and extracted into chloroform which was dried over $Na_2SO_4$ and evaporated to afford 1.37 g (100%) of a white solid, m.p. 120°–123° C. TLC (15% $CH_3OH$/85% $CHCl_3$) $R_f$=0.52.

Anal ($C_{20}H_{36}N_4O_3$·0.25 $H_2O$).
Calcd: C, 62.39; H, 9.55; N, 14.55.
Found: C, 62.53; H, 9.55; N, 14.55.

EXAMPLE 14

H-L-(1-Imidazolyl)Ala Amide of (2S,3R,4S)-2-Amino-1-cyclohexyl-3,4-dihydroxy-6-methylheptane Using the procedure of Example 13 with the resultant compound from Example 9 gave the desired product, m.p. 82°–86° C. TLC (15% methanol/85% $CHCl_3$) $R_f$=0.33; $^1$H NMR ($CDCl_3$) δ7.53 (1H,s), 7.42 (1H,d), 7.10 (1H,s), 6.95 (1H,S), 4.46 (1H,dd), 4.30 (1H,ddd), 4.23 (1H,dd), 3.74 (1H,dd), 3.15–3.30 (2H,m), 0.96 (3H,d), 0.89 (3H,d).

Anal ($C_{20}H_{36}N_4O_3$).

Calcd: C, 63.13; H, 9.54; N, 14.72.

Found: C, 63.33; H, 9.68; N, 14.45.

EXAMPLE 15

H-L-(2-Thienyl)Ala Amide of (2S,3R,4S)-2-Amino-1-cyclohexyl-3,4-dihydroxy-6-methylheptane Using the procedure of Example 13 with the resultant compound from Example 10 gave the desired product as a foam. TLC (10% methanol/90% chloroform) $R_f$=0.48.

Anal ($C_{21}H_{36}N_2O_3S.0.25\ H_2O$)

Calcd: C, 62.89; H, 9.17; N, 6.98.

Found: C, 62.95; H, 9.19; N, 6.61.

EXAMPLE 16

H-Nle Amide of (2S,3R,4S)-2-Amino-1-cyclohexyl-3,4-dihydroxy-6-methylheptane

Using the procedure of Example 13 with the resultant compound from Example 11 gave the desired product as a white solid after recrystallization from methylene chloride/hexane, m.p. 146°–148° C. TLC (15% methanol/85% chloroform) $R_f$=0.50.

Anal ($C_{20}H_{40}N_2O_3$).

Calcd: C, 67.37; H, 11.31; N, 7.86.

Found: C, 67.56, H, 11.22; N, 7.85.

EXAMPLE 17

H-Met-Amide of (2S,3R,4S)-2-Amino-1-cyclohexyl-3,4-dihydroxy-6-methylheptane

Using the procedure of Example 13 with the resultant compound from Example 12 gave the desired product.

EXAMPLE 18

H-L-(4-Thiazolyl)Ala Amide of (2S,3R,4S)-2-Amino-1-cyclohexyl-3,4-dihydroxyhexane Using the procedure of Example 7 but replacing (2S,3R,4S)-2-[(tert-butyloxycarbonyl)amino]-1-cyclohexyl-3,4-dihydroxy-6-methylheptane with (2S,3R,4S)-2-[(tertbutyloxycarbonyl)amino]-1-cyclohexyl-3,4-dihydroxyhexane (Luly et al., *J. Med. Chem.* 1988, 31, 2264) gave the desired amine as a foam.

Anal ($C_{18}H_{31}N_3O_3S.0.5\ H_2O$).

Calcd: C, 57.12; H, 8.52; N, 11.10.

Found: C, 57.27; H, 8.19; N, 11.07.

EXAMPLE 19

H-L-(4-Thiazolyl)Ala Amide of (4S,5R,6S)-6-Amino-4,5-dihydroxy-2,8-dimethylnonane Using the procedure of Example 7 but replacing (2S,3R,4S)-2-[(tert-butyloxycarbonyl)amino]-1-cyclohexyl-3,4-dihydroxy-6-methylheptane with (4S,5R,6S)-6-[(tertbutyloxycarbonyl)amino-4,5-dihydroxy-2,8-dimethylnonane (Luly et al., *J. Org. Chem.* 1988, 53, 6109) gave the desired product as an oil. TLC (10% $CH_3OH$/90% $CHCl_3$) $R_f$=0.18.

EXAMPLE 20

(4R)-3-(3-Phenylpropionyl)-4-(2-propyl)-oxazolidine-2-one.

To a stirred solution of 4-(2-propyl)-oxazolidine-2-one in anhydrous tetrahydrofuran (250 ml) under a nitrogen atmosphere at −78° C. were added in a dropwise fashion a solution of n-butyllithium in hexane (50 ml, 77.4 mmol) over 5 to 10 min. After stirring an additional 20 min at −78° C. 3-phenylpropionyl chloride (12.7 ml, 85.2 mmol) was added neat. The reaction was warmed to room temperature and stirred 1 to 2 h. The reaction was quenched by adding 100 ml of saturated aqueous ammonium chloride and the volatiles removed by rotary evaporation. The resulting aqueous residue was extracted three times with ether and the combined organic phases were washed with brine, dried ($Na_2SO_4$), filtered and concentrated in vacuo. Recrystallization from hexanes/ethyl acetate provided the title compound (16.6 g, 82%); m.p. 86.5° to 87.5° C. Mass spectrum: $(M+NH_4)^+$=279, $(M+H)^+$=262.

EXAMPLE 21

(4R)-3-(2R)-3-t-Butyloxycarbonyl-2-benzylpropionyl]-4-(2-propyl)-oxazolidine-2-one.

To a stirred solution of the product resulting from Example 20 (2.28 g, 8.72 mmol), in anhydrous tetrahydrofuran (30 ml) under a nitrogen atmosphere at −78° C. was added a solution of sodium hexamethyldisilylamide (9.6 ml, 9.59 mmol) in tetrahydrofuran. After stirring for 30 min at. −78° C, t-butyl bromoacetate (2.21 g, 11.34 mmol) was added in anhydrous tetrahydrofuran and the resulting solution stirred 1 h at −78° C. The reaction was quenched by adding 20 ml of saturated aqueous ammonium chloride and partitioned between water and ether. The aqueous layer was drawn off and extracted with ether. The combined organic phases were washed with 10% aqueous HCl, saturated aqueous $NaHCO_3$, and brine, dried ($Na_2SO_4$), filtered, and concentrated in vacuo. Recrystallization from acetone/hexanes provided the desired purified product (2.59 g, 79%); m.p. 167°–168° C. Mass spectrum: $(M+NH_4)^+$=393, $(M+H)^+$=376.

EXAMPLE 22

Benzyl (2R)-3-t-Butyloxycarbonyl-2-benzylpropionate.

To a stirred solution of dry benzyl alcohol (0.55 ml, 5.33 mmol) in anhydrous tetrahydrofuran (18 ml) under a nitrogen atmosphere at 0° C. was added a hexane solution of N-butyllithium (2.58 ml; 4.00 mmol). To this solution was added the product from Example 21 in anhydrous tetrahydrofuran (10 ml). After stirring 1 h at 0° C. the reaction was quenched by adding excess saturated aqueous ammonium chloride. The volatiles were removed by rotary evaporation and the resulting aqueous residue extracted two times with ether. The combined organic layers were washed with brine, dried (Na$_2$SO$_4$), filtered, and concentrated in vacuo provided an oil which was purified by chromatography on SiO$_2$(15% ethyl acetate/hexanes) to provide the desired product (0.89 g, 94%) as a colorless oil. Mass spectrum: (M)$^+$ = 354.

EXAMPLE 23

Benzyl (2R)-3-Carboxy-2-benzylpropionate.

The product from Example 22 (0.52 g, 1.47 mmol) was dissolved in a 1:1 (v:v) solution (6 ml) of trifluoroacetic acid and dichloromethane and stirred at room temperature for 1 h. The volatiles were removed in vacuo to provide the title compound (0.437 g, 100%) as an oil which crystallized on standing. The unpurified material was of sufficient purity to employ in subsequent steps. Mass spectrum: (M)$^+$ = 298.

EXAMPLE 24

Benzyl (2R)-2-Benzyl-3-(4-trifluoroethylpiperazin-1-ylcarbonyl)propionate.

The resultant acid from Example 23 (0.500 g, 1.68 mmol) in CH$_2$Cl$_2$ (7 ml) at −10° C. was treated with N-methylmorpholine (0.20 ml, 1.82 mmol) and then isobutyl chloroformate (0.22 ml, 1.68 mmol). After 5 min 1-trifluoroethylpiperazine (0.30 g, 1.78 mmol) was added and the mixture was stirred at −10° C. for 15 min and then at room temperature for 2 h. The solvent was evaporated and the residue was taken up in ethyl acetate which was washed with saturated NaHCO$_3$ solution, water and brine, and then dried over Na$_2$SO$_4$ and evaporated. Chromatography of the residue on silica gel with 20–33% ethyl acetate in hexane provided 0.61 g (81%) of an oil. $^1$H NMR (CDCl$_3$) δ7.10–7.40 (m,10H), 5.15 (d,1H), 5.05 (d,1H), 3.25–3.70 (m,5H), 3.04 (dd,1H), 2.97 (q,2H), 2.81 (dd,1H), 2.72 (dd,1H), 2.60 (m,4H), 2.32 (dd,1H).

EXAMPLE 25

(2R)-2-Benzyl-3-(4-trifluoroethylpiperazine-1-ylcarbonyl)propionic Acid.

The resultant compound from Example 24 (610 mg), and 10% palladium on carbon (300 mg) in methanol were stirred under an H$_2$ atmosphere for 2 h. Filtration and solvent evaporation afforded 470 mg (96%) of a solid, m.p. 96°–98° C.

EXAMPLE 26

Benzyl (2R)-2-Benzyl-3-[(4-cyclopropylpiperazin-1-yl)carbonyl]propionate

Using the procedure of Example 24 and replacing 1-trifluoroethylpiperazine with 1-cyclopropylpiperazine gave the desired product. $^1$H NMR (CDCl$_3$) δ7.10–7.34 (5H,m), 5.11 (2H,dd), 3.51 (2H,m), 3.31 (3H,m), 3.04 (1H,dd), 2.74 (2H,m), 2.52 (3H,m), 2.35 (1H,dd), 0.47 (2H,m), 0.42 (2H,m).

EXAMPLE 27

(2R)-2-Benzyl-3-(4-cyclopropylpiperazin-1-yl)carbonyl]propionic Acid

Using the procedure of Example 25 with the resultant compound from Example 26 gave the desired product.

EXAMPLE 28

Benzyl (2R)-2-Benzyl-3-[(2-pyridin-2-ylethyl)methylaminocarbonyl]propionate.

Using the procedure of Example 24 but replacing 1-trifluoroethylpiperazine with 2-(2-methylaminoethyl)pyridine provided the desired product as an oil. $^1$H NMR (CDCl$_3$) δ8.48 (m,1H), 7.57 (m,1H), 6.95–7.40 (m,12H), 5.00–5.20 (m,2H), 2.87, 2.82 (2s,total 3H), 2.31, 2.18 (2dd,total 1H).

EXAMPLE 29

(2R)-2-Benzyl-3-[(2-pyridin-2-ylethyl)methylaminocarbonyl]propionic Acid.

Prepared from the resultant compound of Example 28 according to the procedure of Example 25. $^1$H NMR (CDCl$_3$) δ8.49 (m,1H), 7.58 (m,1H), 6.95–7.32 (m,7H), 2.87, 2.72 (2s,total 3H).

EXAMPLE 30

Benzyl (2R)-2-Benzyl-3-[(N-pyridin-4-yl)methylaminocarbonyl]propionate.

Using the procedure of Example 24 but replacing 1-trifluoroethylpiperazine with 4-methylaminopyridine provided the desired product. $^1$H NMR (CDCl$_3$) δ8.6 (m,2H), 7.4–7.0 (m,12H), 5.1 (q,2H), 3.3 (m,1H), 3.2 (s,3H), 3.0 (dd,1H), 2.7 (dd,1H), 2.6 (dd,1H), 2.25 (dd,1H).

EXAMPLE 31

(2R)-2-Benzyl-3-(N-pyridin-4-yl)methylaminocarbonyl]propionic Acid.

Prepared from the resultant compound of Example 30 according to the procedure of Example 25, m.p. 88°–92° C.

EXAMPLE 32

Benzyl (2S)-2-(4-morpolinyl)-3-phenylpropionate.

2,5-Dihydrofuran (0.78 ml, 10.3 mmol) in methanol (4 ml) and CH$_2$Cl$_2$ (16 ml) at −60° C. was treated with ozone until a blue color persisted, and the excess ozone was removed under a stream of N$_2$. To this solution was added NaCNBH$_3$ (456 mg, 7.26 mmol). After 15 min at −60° C., H-Phe-OBn p-toluenesulfonic acid salt (2.22 g, 5.19 mmol) in methanol (20 ml) was added over 5 min, and the mixture was stirred at −60° C. for 15 min and at 0° C. for 20 h. The mixture was quenched with acetic acid (0.30 ml, 5.2 mmol), stirred at 0° C. for 30 min and the solvent was evaporated. The residue was taken up in saturated NaHCO$_3$ solution and extracted into CH$_2$Cl$_2$ which was dried over Na$_2$SO$_4$ and evaporated. Chromatography of the residue on silica gel with 20% ethyl acetate in hexane afforded 1.374 g (81%) of an oil. $^1$H NMR (CDCl$_3$) δ7.10–7.35 (m,10H), 5.03 (s,2H), 3.62–3.75 (m,4H), 3.48 (dd,1H), 3.08 (dd,1H), 2.97 (dd,1H), 2.58–2.80 (m,4H).

EXAMPLE 33

(2S)-2-(4-Morpholinyl)-3-phenylpropionic Acid.

Prepared from the resultant compound of Example 32 according to the procedure of Example 25. $^1$H NMR (CD$_3$OD) δ7.15–7.35 (m,5H), 3.78 (m,4H), 3.57 (m,1H), 3.12 (m,2H), 3.03 (m,4H).

EXAMPLE 34

Benzyl (2R)-2-Benzyl-3-chloromethylcarbonylpropionate.

The resultant acid from Example 23 (500 mg, 1.68 mmol) in $CH_2Cl_2$ (8 ml) at 0° C. was treated with oxalyl chloride (0.160 ml, 1.83 mmol) and dimethylformamide (0.0065 ml). After 2 h at 0° C., the solvent was evaporated and the residue was dissolved in ether (6 ml), cooled to 0° C. and treated with an ether solution of $CH_2N_2$. After 2 h at 0° C. the solvent was evaporated and the residue was dissolved in ether (6 ml), cooled to −10° C., and treated with 4.0M HCl/dioxane (0.6 ml, 2.4 mmol). After 1 h the solvent was evaporated and the residue was chromatographed on silica gel with 10% ethyl acetate in hexane to afford 476.8 mg (83%) of a colorless oil. $^1H$ NMR ($CDCl_3$) $\delta$7.08–7.40 (m,10H), 5.12 (d,1H), 5.08 (d,1H), 4.02 (s,2H), 3.30 (m,1H), 3.10 (dd,1H), 2.97 (dd,1H), 2.78 (dd,1H), 2.55 (dd,1H).

EXAMPLE 35

Benzyl (2R)-2-Benzyl-3-thiazol-4-ylpropionate.

The resultant compound from Example 34 (476.8 mg, 1.44 mmol) and thioformamide (176 mg, 2.88 mmol) in acetone (6 ml) were stirred at room temperature for 108 h. N-methylmorpholine (0.16 ml, 1.40 mmol) was added and after 20 min the mixture was diluted with ether, filtered, evaporated, and chromatographed on silica gel with 20% ethyl acetate in hexane to afford 369 mg (76%) of an oil. $^1H$ NMR ($CDCl_3$) $\delta$8.70 (d,1H), 7.05–7.35 (m,10H), 6.90 (d,1H), 5.00 (d,1H), 4.95 (d,1H), 3.28–3.35 (m,1H), 3.19 (dd,1H), 2.95–3.10 (m,2H), 2.88 (dd,1H).

EXAMPLE 36

(2R)-2-Benzyl-3-thiazol-4-ylpropionic Acid.

The resultant compound from Example 35 (364 mg) was stirred for 2 h in 30% HBr in acetic acid (5 ml). The solvent was evaporated and the residue was dissolved in 1M HCl and washed with ether. The aqueous phase was adjusted to pH 4 with solid $NaHCO_3$ and extracted with chloroform which was dried over $Na_2SO_4$ and evaporated to afford 186.5 mg (70%) of an oil. $^1H$ NMR ($CDCl_3$) $\delta$8.78 (d,1H), 7.15–7.35 (m,5H), 6.99 (d,1H), 3.00–3.30 (m,4H), 2.81 (dd,1H).

EXAMPLE 37

Benzyl (2R)-2-Benzyl-5-tert-butylmercapto-4-oxopentanoate.

To tert-butylmercaptan (0.11 ml) in dimethylformamide (5 ml) at 0° C. was added potassium bis(trimethylsilyl)amide in toluene (1.80 ml, 0.90 mmol, 0.5M) followed by the resultant compound from Example 34 (259.6 mg, 0.785 mmol) in dimethylformamide (3 ml). After 16 h at room temperature the mixture was diluted with ethyl acetate, washed with water and brine, then dried over $Na_2SO_4$ and evaporated. Chromatography of the residue on silica gel with 10% ethyl acetate in hexane afforded 219.6 mg (73%) of a colorless oil. $^1H$ NMR ($CDCl_3$) $\delta$7.10–7.40 (m,10H), 5.07 (s,2H), 3.25 (s,2H), 3.18–3.29 (m,1H), 2.97–3.07 (m,2H), 2.78 (dd,1H), 2.71 (dd,1H), 1.25 (s,9H).

EXAMPLE 38

Benzyl (2R)-2-Benzyl-5-tert-butylsulfinyl-4-oxopentanoate.

The resultant compound from Example 37 (44.4 mg, 0.115 mmol) in $CH_2Cl_2$(2 ml) at −10° C. was treated with meta-chloroperbenzoic acid (25.0 mg, 0.116 mmol, 80% pure). After 2 h at −10°-0° C. the solvent was evaporated and the residue was dissolved in ethyl acetate which was washed with 1:1 10% $Na_2SO_4$ solution/saturated $NaHCO_3$ solution, saturated $NaHCO_3$ solution and brine, and then dried over $Na_2SO_4$ and evaporated to afford 46.0 mg (99%) of a colorless oil. $^1H$ NMR ($CDCl_3$) $\delta$7.05–7.40 (m,10H), 5.08 (m,2H), 3.36–3.53 (m,2H), 3.30 (m,1H), 2.95–3.18 (m,2H), 2.80 (2dd,total 1H), 2.69 (2dd,total 1H), 1.24 (s,9H).

EXAMPLE 39

Benzyl (2R)-2-Benzyl-5-tert-butylsulfonyl-4-oxopentanoate.

The resultant compound from Example 37 (171.9 mg, 0.447 mmol) in $CH_2Cl_2$ (5 ml) was treated with meta-chloroperbenzoic acid (290 mg, 1.34 mmol, 80% pure). After 75 min at room temperature the product was isolated as described in Example 38 to afford 184.0 mg (59%) of a colorless oil. $^1H$ NMR ($CDCl_3$) $\delta$7.08–7.35 (m,10H), 5.07 (s,2H), 3.98 (d,1H), 3.88 (d,1H), 3.23–3.33 (m,1H), 3.18 (dd,1H), 3.03 (dd,1H), 2.88 (dd,1H), 2.82 (dd,1H), 1.38 (s,9H).

EXAMPLE 40

(2R)-2-Benzyl-5-tert-butylsulfinyl-4-oxopentanoic Acid.

Prepared from the resultant compound from Example 38 according to the procedure of Example 25. $^1H$ NMR ($CDCl_3$) $\delta$7.15–7.35 (m,5H), 1.23 (s,9H).

EXAMPLE 41

(2R)-2-Benzyl-5-tert-butylsulfonyl-4-oxopentanoic Acid.

Prepared from the resultant compound from Example 39 according to the procedure of Example 25. $^1H$ NMR ($CDCl_3$) $\delta$7.15–7.35 (m,5H), 3.94 (d,1H), 3.88 (d,1H), 2.90–3.30 (m,3H), 2.70–2.85 (m,2H), 1.39 (s,9H).

EXAMPLE 42

Benzyl (2R)-2-Benzyl-5-morpholin-4-yl-4-oxopentanoate.

The resultant compound from Example 34 (610 mg, 1.84 mmol) in dimethylformamide (10 ml) was treated with NaI (33 mg, 0.22 mmol) and morpholine (0.60 ml, 6.88 mmol). After 2 h the mixture was diluted with ethyl acetate, washed with water and brine, and then dried over $Na_2SO_4$, and evaporated. Chromatography of the residue on silica gel with 60% ethyl acetate/40% hexane afforded 460 mg (65%) of an oil. $^1H$ NMR ($CDCl_3$) $\delta$7.05–7.40 (m,10H), 5.11 (d,1H), 5.06 (d,1H), 3.68 (m,4H), 3.22–3.32 m,1H), 3.15 (d,1H), 3.08 (d,1H), 3.05 (m,1H), 2.87 (dd,1H), 2.77 (dd,1H), 2.35–2.50 (m,5H).

EXAMPLE 43

(2R)-2-Benzyl-5-morpholin-4-yl-4-oxopentanoic Acid.

Prepared from the resultant compound from Example 42 according to the procedure of Example 25. $^1$H NMR (CDCl$_3$) δ7.15–7.35 (m,5H), 3.60–3.75 (m,4H).

Methyl α-Benzylacrylate.

α-Benzylacrylic acid (1.00 g, 6.17 mmol) in methanol (20 ml) was treated with BF$_3$.Et$_2$O (2 ml). The mixture was heated to reflux for 14 h, cooled, and poured into saturated NaHCO$_3$ solution. Extraction with ether followed by drying over Na$_2$SO$_4$ and evaporation afforded 1.03 g (95%) of a mobile oil. $^1$H NMR (CDCl$_3$) δ7.17–7.35 (m,5H), 6.23 (m,1H), 5.47 (m,1H), 3.74 (s,3H), 3.63 (s,2H).

EXAMPLE 45

Methyl (2RS)-2-Benzyl-3-(N-methoxyl-N-methylamino)propionate.

The resultant compound from Example 44 (800 mg, 4.54 mmol), N-methyl-O-methylhydroxylamine hydrochloride (0.57 g, 5.4 mmol), and NaHCO$_3$ (0.46 g, 5.48 mmol) in dimethylsulfoxide (5 ml) were heated at 130° C. for 20 h. The mixture was diluted with ethyl acetate, washed with water, saturated NaHCO$_3$ solution and brine, and then was dried over Na$_2$SO$_4$ and evaporated. Chromatography of the residue on silica gel with 10% ethyl acetate in hexane afforded 226 mg (21%) of a mobile oil. $^1$H NMR (CDCl$_3$) δ 7.10–7.30 (m,5H), 3.60 (s,3H), 3.47 (s,3H), 2.80–3.10 (m,4H), 2.60 (dd,1H), 2.55 (s,3H).

EXAMPLE 46

Methyl (2RS)-2-Benzyl-3-pyrazol-1-ylpropionate.

Using the procedure of Example 45 but replacing N-methyl-O-methylhydroxylamine hydrochloride and NaHCO$_3$ with pyrazole provided the desired product as an oil. $^1$H NMR (CDCl$_3$) δ7.52 (d,1H), 7.10–7.35 (m,6H), 6.10 (dd,1H), 4.38 (dd,1H), 4.24 (dd,1H), 3.57 (s,3H), 3.37 (m,1H), 2.98 (dd,1H), 2.82 (dd,1H).

EXAMPLE 47

(2RS)-2-Benzyl-3-pyrazol-1-ylpropionic Acid.

The resultant compound from Example 46 (100.0 mg, 0.409 mmol) in dioxane (2 ml) at 0° C. was treated with LiOH.H$_2$O (22.0 mg, 0.524 mmol) in water (1 ml). After 1 h at 0° C. and 30 min at room temperature the solvent was evaporated and the residue was taken up in water, the pH was adjusted to pH 3–4, and the mixture was extracted with CHCl$_3$ which was dried over Na$_2$SO$_4$ and evaporated to afford 96 mg (100%) of a solid. $^1$H NMR (CDCl$_3$) δ7.56 (d,1H), 7.10–7.35 (m,6H), 6.26 (dd,1H), 4.30 (m,2H), 3.34 (m,1H), 3.12 (dd,1H), 2.72 (dd,1H).

EXAMPLE 48

(2RS)-2-Benzyl-3-(N-methoxyl-N-methylamino)propionic Acid.

Using the procedure of Example 47 with the resultant compound from Example 45 gave the desired product. $^1$H NMR (CDCl$_3$) δ7.10–7.35 (m,5H), 3.58 (s,3H), 2.62 (s,3H).

EXAMPLE 49

Methyl (2RS)-2-Benzyl-3-imidazol-1-ylpropionate

Using the procedure of Example 46 and replacing pyrazole with imidazole gave the desired product as an oil. TLC (5% methanol/95% chloroform) R$_f$=0.28; $^1$H NMR (CDCl$_3$) δ7.42 (1H,s), 7.10–7 35 (5H,m), 7.03 (1H,s), 6.83 (1H,s), 4.23 (1H,dd), 4.02 (1H,dd), 3.59 (3H,s), 3.07–3.18 (1H,m), 3.02 (1H,dd), 2.77 (1H,dd).

EXAMPLE 50

(2RS)-2-Benzyl-3-imidazol-1-ylpropionic Acid

Using the procedure of Example 47 with the resultant ester from Example 49 gave the desired product as a solid, m.p. 159°–163° C. $^1$H NMR (CD$_3$OD) δ4.35 (1H,dd), 4.19 (1H,dd), 3.20–3.00 (1H,m), 3.02 (1H,dd), 2.81 (1H,dd).

EXAMPLE 51

Benzyl (2R)-2-Benzyl-3-[N-(2-hydroxylethyl)-N-methyl]-aminocarbonylpropionate.

Using the mixed anhydride coupling procedure of Example 24 with the resultant compound from Example 23 and N-methyl-ethanolamine gave the desired compound in 90% yield after recrystallization from 1:4 ethyl acetate/hexane, m.p. 77°–78 ° C.; TLC (15% CH$_3$OH/85% CHCl$_3$) R$_f$=0.61;. $^1$H NMR (CDCl$_3$) δ7.10–7.40 (m,10H), 5.10 (m,2H), 3.00, 2.92 (s,total 3H).

Anal (C$_{21}$H$_{25}$NO$_4$)
Calcd: C, 70.96; H, 7.09; N, 3.94.
Found: C, 71.15; H, 7.10; N, 3.67.

EXAMPLE 52

Benzyl (2R)-2-Benzyl-3-[(2-morpholin-4-ylethyl)methylaminocarbonyl]propionate.

To benzyl (2R)-2-benzyl-3-[N-(2-hydroxyethyl)-N-methyl]aminocarbonylpropionate (110 mg, 0.31 mmol) in CH$_2$Cl$_2$ (2 ml) at −78° C. was added triethylamine (0.070 ml, 0.50 mmol) and methanesulfonyl chloride (0.036 ml, 0.047 mmol). After 1 h morpholine (0.085 ml, 0.97 mmol) was added and the mixture was stirred at room temperature for 5 h. The solvent was evaporated and the residue was suspended in ethyl acetate, washed with saturated NaHCO$_3$ solution, water and brine, then dried over Na$_2$SO$_4$ and evaporated. Chromatography of the residue on silica gel with 2:1 ethyl acetate in hexane afforded 90.0 mg (68%) of the desired product. $^1$H NMR (CDCl$_3$) δ7.10–7.37 (m,10H), 5.00–5.20 (m,2H), 3.60–3.73 (m,4H), 2.94, 2.90 (2s,total 3H).

EXAMPLE 53

(2R)-2-Benzyl-3-[(2-morpholin-4-ylethyl)methylaminocarbonyl]propionic Acid.

Using the procedure of Example 25 with the resultant compound from Example 52 gave the desired product. $^1$H NMR (CDCl$_3$) δ7.17–7.33 (m,5H), 3.60–3.70 (m,4H), 2.92, 2.86 (2s,total 3H).

EXAMPLE 54

Benzyl (2R)-2-Benzyl-3-[(2-imidazol-1-ylethyl)methylaminocarbonyl]propionate.

Using the procedure of Example 52 and replacing morpholine with imidazole and changing stirring at room temperature for 5 h to heating at reflux for 4 h gave, after chromatography on silica gel with 0.5% methanol in chloroform, the desired product. $^1$H NMR (CDCl$_3$) δ7.42 (s,1H), 7.00–7.40 (m,11H), 6.89 (s,1H), 5.18 (d,1H), 5.08 (s,1H), 4.05 (m,2H), 3.61 (m,1H), 3.50 (m,1H), 3.32 (m,1H), 3.08 (m,1H), 2.60–2.85 (m,2H), 2.59 (s,3H), 2.27 (dd,1H).

EXAMPLE 55

(2R)-2-Benzyl-3-[(2-imidazol-1-ylethyl)methylaminocarbonyl]propionate.

Using the procedure of Example 25 with the resultant compound from Example 54 gave the desired product. $^1$H NMR (CDCl$_3$) δ7.83 (s,1H), 7.15–7.32 (m,5H), 7.14 (s,1H), 6.93 (s,1H), 3.30 (m,2H), 3.09 (m,1H), 2.60–2.78 (m,2H), 2.60 (s,3H).

EXAMPLE 56

Benzyl (2R)-2-Benzyl-3-[2-(4-methylpiperazin-1-ylethyl)methylaminocarbonyl]propionate.

Using the procedure of Example 52 and replacing morpholine with 1-methylpiperazine and changing stirring at room temperature for 5 h to heating at reflux for 4 h gave, after chromatography on silica gel with 1–3% methanol in chloroform, the desired product. $^1$H NMR (CDCl$_3$) δ7.10–7.35 (m,10H), 5.00–5.20 (m,2H), 2.93, 2.89 (2s,total 3H), 2.28 (2s,total 3H).

EXAMPLE 57

(2R)-2-Benzyl-3-[2-(4-methylpiperazin-1-ylethyl)methylaminocarbonyl]propionic Acid.

Using the procedure of Example 25 with the resultant compound from Example 56 gave the desired product. $^1$H NMR (CDCl$_3$) δ7.13–7.32 (m,5H), 2.92, 2.88 (2s,total 3H), 2.31, 2.33 (2s,total 3H).

EXAMPLE 58

Benzyl (2R)-2-Benzyl-3-[(2-pyrazol-1-ylethyl)methylaminocarbonyl]propionate.

Using the procedure of Example 52 and replacing morpholine with pyrazole and changing stirring at room temperature for 5 h to heating at reflux for 4 h gave, after chromatography on silica gel with 0.5% methanol in chloroform, the desired product. $^1$H NMR (CDCl$_3$) δ7.51, 7.40(2d, total 1H), 7.18–7.38(m,10H), 7.08–7.17(m,1H), 6.21, 6.13(2dd, total 1H), 4.99–5.20(4d, total 2H), 2.78, 2.52(2S, total 3H).

EXAMPLE 59

(2R)-2-Benzyl-3-[(2-pyrazol-1-ylethyl)methylaminocarbonyl]propionic Acid.

Using the procedure of Example 25 with the resultant compound from Example 58 gave the desired product. $^1$H NMR (CDCl$_3$) δ7.62(d,1H), 7.51, 7.45(2d, total 1H), 7.15–7.37(m,5H), 6.22, 6.19(2dd, total 1H), 2.82, 2.49(2s, total 3H).

EXAMPLE 60

Benzyl α-Benzylacrylic

α-Benzylacrylic acid (2.20 g, 13.6 mmol) in dry ether (40 mL) was treated with dicyclohexylcarbodiimide (2.60 g, 12.6 mmol), benzyl alcohol (1.30 mL, 12.6 mmol) and 4-dimethylaminopyridine (0.310 g, 2.54 mmol). After stirring at room temperature for 44 h, the mixture was filtered and evaporated. Chromatography of the residue on silica with 5% ethyl acetate in hexane afforded 2.70 g (85%) of a colorless oil. TLC (20% ethyl acetate/80% hexane) R$_f$=0.59; $^1$H NMR (CDCl$_3$) δ7.15–7.40 (10H,m), 6.28 (1H,m), 5.49 (1H,m), 5.17 (2H,s), 3.67 (2H,s).

EXAMPLE 61

Benzyl 3-Acetylmercapto-2-benzylpropionate

The resulting compound from Example 60 (7.00 g, 27.7 mmol) in dry ether (10 mL) was treated with thiolacetic acid (3.00 mL, 42.0 mmol) and pyridine (2.30 mL, 28.4 mmol). After 114 h at room temperature the mixture was evaporated and chromatographed on silica gel (500 g) with 5–10% ethyl acetate in hexanes to afford 8.34 g (92%) of a mobile oil. TLC (20% ethyl acetate/80% hexane) R$_f$=0.40; $^1$H NMR (CDCl$_3$) δ7.05–7.40 (10H,m), 5.05 (2H,s), 2.87–3.20 (5H,m), 2.31 (3H,s).

Anal (C$_{19}$H$_{20}$O$_3$S.0.5 H$_2$O)
Calcd: C, 67.63; H, 6.27
Found: C, 67.98; H, 6.04.

EXAMPLE 62

2-Benzyloxycarbonyl -3-phenyl-1-propylsulfonyl Chloride.

Chlorine was bubbled into a mixture of the resultant compound from Example 61 (8.34 g, 25.4 mmol) in water (250 mL) for 30 min at room temperature followed by nitrogen which was bubbled through the mixture for 15 min. The mixture was extracted with methylene chloride which was dried over MgSO$_4$ to afford 8.55 g (95%) of an oil which was used without further purification. $^1$H NMR (CDCl$_3$) δ7.05–7.45 (10H,m), 5.13 (2H,s), 4.21 (1H,dd), 3.67 (1H,dd), 3.46–3.57 (1H,m), 3.16 (1H,dd), 2.94 (1H,dd).

EXAMPLE 63

Benzyl 2-Benzyl-3-[[2-pyridine-2 -ylethyl(methyl)amino]sulfonyl]propionate.

To the resultant compound from Example 62 (1 mmol) in methylene chloride (10 mL) at -10° C. was added triethylamine (1.2 mmol) and 2-(2-methylaminoethyl)pyridine (1 mmol). After 30 min the mixture was evaporated, suspended in ethyl acetate, washed with saturated NaHCO$_3$ solution, water, and brine, and then dried over Na$_2$SO$_4$ and evaporated. Chromatography of the residue on silica gel afforded the desired product.

EXAMPLE 64

2-Benzyl-3-[[2-pyridin-2-ylethyl(methyl)amino]sulfonyl]propionic Acid.

Using the procedure of Example 25 with the resultant compound from Example 63 gave the desired product as a foam. TLC (15% CH$_3$OH/95% CHCl$_3$) Rf=0.29.

EXAMPLE 65

1-Benzyloxycarbonyl-3-hyfroxyazetidine.

1-Diphenylmethyl-4-hydroxyazetidine (1.00 g, 4.18 mmol) and 10% Pd/C in methanol (10 mL) were stirred under a hydrogen atmosphere for 20 h. The mixture was filtered and evaporated, and the residue was dissolved in methylene chloride and cooled to 0° C. After addition of triethylamine (0.64 mL, 4.57 mmol) and benzyl chloroformate (0.60 mL, 4.20 mmol), the mixture was stirred at room temperature for 90 min. The mixture was evaporated, taken up in ethyl acetate, washed with 2M HCl, saturated $NaHCO_3$ solution and brine, and then dried over $Na_2SO_4$ and evaporated. Chromatography of the residue on silica gel (120 g) with 50–60% ethyl acetate in hexane. afforded 0.376 g (43%) of a colorless oil. TLC (50% ethyl acetate/50% hexane) $R_f=0.13$; $^1H$ NMR ($CDCl_3$) δ 7.29–7.39 (5H,m), 5.10 (2H,s), 4.59–4.70 (1H,m), 4.26 (1H,dd), 4.23 (1H,dd), 3.91 (1H,dd), 3.88 (1H,dd), 2.15 (1H,d).

EXAMPLE 66

3-Acetylmercapto-1-benzyloxycarbonaylazetidine.

To triphenylphosphine (4.40 g, 16.8 mmol) in tetrahydrofuran (25 mL, THF) at −78° C. was added diethylazodicarboxylate (2.60 mL, 16.5 mmol) in THF (15 mL). After 7 min thiolacetic acid (1.25 mL, 17.5 mmol) in THF (15 mL) was added followed by, after 7 min, the resultant compound from Example 65 (2.789 g, 13.46 mmol). The mixture was stirred at −78° C. for 1 h and then at room temperature for 20 h, and was then evaporated and chromatographed on silica gel (300 g) with 20% ethyl acetate in hexane affording 3.250 g (91%) of a white solid, m.p. 94.5–95.5° C. TLC (20% ethyl acetate/80% hexane) $R_f=0.17$; $^1H$ NMR ($CDCl_3$) δ7.28–7.41 (5H,m), 5.09 (2H,s), 4.48 (1H,d), 4.44 (1H,d), 4.15–4.26 (1H,m), 3.92 (1H,d), 3.89 (1H,d) 2.34 (3H,s). Anal ($C_{13}H_{15}NO_3S$). Calcd: C, 58.85; H, 5.70, N, 5.28. Found: C, 58.81; H, 5.70; N, 5.26.

EXAMPLE 67

Methyl 2-Benzyl-3-(1-benzyloxvcarbonylazetidin-3-ylmercapto)propionate.

A solution of sodium methoxide in methanol (3mL) prepared with sodium bis(trimethylsilyl)amide (0.75 mL, 0.75 mmol, 1.0 M in THF) was added to the resultant compound from Example 66 (205.0 mg, 0.773 mmol) in methanol (3 mL). After 45 min, methyl α-benzylacrylate (150.0 mg, 0.851 mmol) in methanol (2 mL) was added. After 45 min the reaction was quenched with 2M HCl (0.38 mL, 0.76 mmol), evaporated, chromatographed on silica gel (30 g) with 20% ethyl acetate in hexane, to afford 280.6 mg (91%) of a colorless oil. TLC (20% ethyl acetate/80% hexane) $R_f=0.13$; $^1H$ NMR ($CDCl_3$) δ 7.10–7.40 (10H,m), 5.08 (2H,s), 4.21–4.33 (2H,m), 3.77–3.90 (2H,m), 3.66 (3H,s), 3.53–3.63 (1H,m), 3.00 (1H,dd), 2.72–2.90 (3H,m), 2.63 (1H,dd).

EXAMPLE 68

Methyl 2-Benzyl-3-(1-benzyloxycarbonylazetidin-3-ylsulfonyl)-propionate.

The resultant compound from Example 67 (276.0 mg, 0.691 mmol) in methanol (6 mL) and water (5 mL) was treated with OXONE (1.27 g, 2.07 mmol). After 14 h the mixture was diluted with methanol, filtered and concentrated to ca. 5 mL. After neutralization with solid $K_2CO_3$ the mixture was extracted into ethyl acetate which was washed with saturated $NaHCO_3$ solution, water, and brine, and then was dried over $Na_2SO_4$ and evaporated to afford 295.9 mg (99%) of a colorless oil. TLC (50% ethyl acetate/50% hexane) $R_f=0.18$; 1H NMR ($CDCl_3$) δ 7.10–7.40 (10H,m), 5.09 (2H,s), 4.22–4.35 (2H,m), 4.25 (1H,dd), 4.12 (1H,dd), 3.80–3.92 (1H,m), 3.73 (3H,s), 3.44 (1H,dd), 3.27–3.38 (1H,m), 3.14 (1H,dd), 2.92 (1H,dd), 2.87 (1H,dd).

EXAMPLE 69

Methyl 2-Benzyl-3-(1-methylazetidin-3ylsulfonyl)propionate.

The resultant compound from Example 68 (270.8 mg) and 10% Pd/C (150 mg) in methanol (6 mL) was treated with formaldehyde in water (0.25 mL, 37% formalin) and stirred under a hydrogen atmosphere for 3 h. The mixture was filtered and evaporated to afford 194.3 mg (99%) of a colorless oil. TLC (15% $CH_3OH/85\%$ $CHCl_3$) $R_f=0.60$; $^1H$ NMR ($CDCl_3$) δ 7.12–7.37 (5H,m), 3.77 (1H,dd), 3.71 (3H,s), 3.56 (1H,dd), 3.38–3.50 (4H,m), 3.26–3.36 (1H,m), 3.12 (1H,dd), 2.96 (1H,dd), 2.88 (1H,dd), 2.32 (3H,s).

EXAMPLE 70

2-Benzyl-3-(1-methylazetidin-3-ylsulfonyl)propionic Acid

The resultant compound from Example 69 (2.120 g, 6.81 mmol) in 2M HCl was stirred at 75° C. for 20 h. The mixture was washed with ether, evaporated with water chasers, and lyophillized to afford 2.075 g (91%) of a white foam. TLC (25% ethyl acetate/25% water/25% acetic acid/25% n-butanol) $R_f=0.50$; $^1H$ NMR ($CD_3OD$) δ7.17–7.35 (5H,m), 3.58–3.68 (2H,m), 2.95 (3H,s).

EXAMPLE 71

Benzyl (2R)-2-Benzyl-3-(2-dimethylaminothiazol-4-yl)propionate.

The resultant compound from Example 34 (182.0 mg, 0.55 mmol) and N,N-dimethylthiourea (86 mg, 0.83 mmol) in acetone (4 ml) were stirred at room temperature for 48 h. The mixture was evaporated, taken up in ethyl acetate, washed with saturated $NaHCO_3$ solution and brine, then dried over $Na_2SO_4$ and evaporated. Chromatography on silica gel (18 g) with 20% ethyl acetate in hexane afforded 194 mg (93%) of an oil. TLC (50% ethyl acetate/50% hexane) $R_f=0.66$; $^1H$ NMR ($CDCl_3$) δ7.10–7.30 (m,10H), 6.06 (s,1H), 5.01 (d,1H), 4.97 (d,1H), 3.15–3.30 (m,2H), 3.04 (s,6H), 2.88–3.00 (m,1H), 2.87 (dd,1H), 2.77 (dd,1H).

EXAMPLE 72

(2R)-2-Benzyl-3-(2-dimethylaminothiazol-4-yl)propionic Acid.

Using the procedure of Example 36 with the resultant compound from Example 71 gave the desired product as an oil. TLC (10% $CH_3OH/90\%$ $CHCl_3$) $R_f=0.47$; $^1H$ NMR ($CDCl_3$) δ7.15–7.35 (m,5H), 5.95 (s,1H), 3.25 (dd,1H), 3.12 (s,6H), 3.00–3.15 (m,1H), 2.60–2.90 (m,3H).

EXAMPLE 73

Benzyl
(2R)-2-Benzyl-3-(2-methylimino-3-methyl-2,3-dihydro-thiazol-4-yl)propionate.

The resultant compound from Example 34 (355.0 mg, 1.07 mmol) and N,N'-dimethylthiourea (98 mg, 0.94 mmol) in acetone (6 ml) were stirred at room temperature for 162 h. The mixture was evaporated, taken up in ethyl acetate, washed with 1.0M $Na_2CO_3$ solution and brine, then dried over $Na_2SO_4$ and evaporated. Chromatography on silica gel (19 g) with 3% methanol in chloroform afforded 319 mg (89%) of an oil. TLC (10% $CH_3OH$/90% $CHCl_3$) $R_f$=0.40; $^1H$ NMR ($CDCl_3$) δ7.10–7.35 (m,10H), 5.51 (s,1H), 5.05 (d,1H), 5.00 (d,1H), 3.12 (s,3H), 2.93–3.08 (m,2H), 2.97 (s,3H), 2.73–2.88 (m,2H), 2.51 (ddd,1H).

EXAMPLE 74

(2R)-2-Benzyl-3-(2-methylimino-3-methyl-2,3-dihydro-thiazol-4-yl)propionic Acid Hydrobromide.

The resultant compound from Example 73 (315 mg, 0.828 mmol) was stirred for 2 h in 30% HBr in acetic acid (5 ml). The solvent was evaporated and the residue was dissolved in water which was washed with ether and lyophillized to afford 310 mg (100%) of the desired product as a foam. $^1H$ NMR ($CD_3OD$) δ7.20–7.35 (m,5H), 6.72 (s,1H), 3.44 (s,3H), 3.08 (s,3H), 2.70–3.20 (m,5H).

EXAMPLE 75

Benzyl
(2R)-2-Benzyl-3-(5.6-dihydroimidazo[2,1-b]thiazol-3-yl)propionate.

Using the procedure of Example 73 but replacing N,N'-dimethylthiourea with 2-imidazolidinethione gave the desired product as an oil. TLC (10% $CH_3OH$/90% $CHCl_3$) $R_f$=0.32; $^1H$ NMR ($CD_3OD$) δ7.15–7.35 (m,10H), 6.42 (s,1H), 5.06 (d,1H), 5.01 (d,1H), 4.15–4.32 (m,4H), 2.70–3.20 (m,4H), 2.77 (ddd,1H).

EXAMPLE 76

(2R)-2-Benzyl-3-(5,6-dihydroimidazo[2,1-b]thiazol-3-yl)propionic Acid Hydrobromide.

Using the procedure of Example 74 with the resultant compound from Example 75 gave the desired product as a foam. TLC (25% ethyl acetate/25% water/25% acetic acid/25%n-butanol) $R_f$=0.51; $^1H$ NMR ($CD_3OD$) δ7.20–7.35 (m,5Hc acid/25%n-butanol) $R_f$=0.51; $^1H$ NMR ($CD_3OD$) δ7.20–7.35 (m,5H), 6.51 (s,1H), 4.32 (s,4H), 3.00–3.15 (m,2H), 2.83–2.95 (m,2H), 2.72 (ddd,1H).

EXAMPLE 77

α-Isocyanato-L-(O-methyl)tyrosine Methyl Ester.

A suspension of (O-methyl)tyrosine methyl ester hydrochloride (6 g) in toluene (125 ml) was heated at 100° C. while phosgene was bubbled into the reaction mixture. After 2 h the mixture became homogeneous and the phosgene was continued for an additional 15 min. The mixture was cooled and evaporated with several benzene chasers to provide the desired product.

EXAMPLE 78

[2-Pyridin-2-ylethyl(methyl)amino]carbonyl(O-methyl)tyrosine Methyl Ester.

To the resultant isocyanate from Example 77 (0.25 g, 1.06 mmol) in methylene chloride (5 mL) was added 2-(2-methylaminoethyl)pyridine (0.15 mL, 1.08 mmol). After 3 h the mixture was chromatographed on silica gel with ethyl acetate to give 0.342 g (87%) of the desired product as a colorless oil. TLC (10% methanol/90% ethyl acetate) $R_f$=0.55; $^1H$ NMR ($CDCl_3$) δ8.44 (1H,d), 7.59 (1H,ddd), 7.08–7.17 (2H,m), 7.05 (2H,d), 6.80 (2H,d), 5.66 (1H,br), 4.68 (1H,dd), 3.78 (3H,s), 3.69 (3H,s), 3.52–3.78 (2H,m), 2.95–3.10 (4H,m), 2.80 (3H,s).

EXAMPLE 79

[2-Pyridin-2-ylethyl(methyl)amino]carbonyl(O-methyl)tyrosine

Using the procedure of Example 47 with the resultant compound from Example 78 gave the desired product as a foam. $^1H$ NMR ($CDCl_3$) δ8.66 (1H,d), 8.28 (1H,dd), 7.79 (1H,d), 7.73 (1H,d), 7.13 (2H,d), 6.81 (2H,d), 5.50 (1H,br), 4.28–4.38 (1H,m), 3.77 (3H,s), 3.00 (3H,s).

EXAMPLE 80

Methyl
(2S)-[[2-Pyridin-2-ylethyl(methyl)aminocarbonyl]oxy]-3-phenylpropionate

To L-phenyllactic acid methyl ester (3 2 g) was added 150 mL of 12.5% phosgene in toluene and 25 drops of dimethylformamide. After stirring at room temperature for 16 h, the solvent was evaporated and the residue was chased several times with benzene. The residue was dissolved in methylene chloride (50 mL), cooled to 0° C., and treated with triethylamine (20 mmol) and 2-(2-methylaminoethyl)pyridine (18 mmol). After 2 h the mixture was evaporated, suspended in ethyl acetate, washed with saturated $NaHCO_3$ solution, water and brine, and then dried over $Na_2SO_4$ and evaporated. Chromatography of the residue on silica gel afforded the desired product. TLC (ethyl acetate) $R_f$=0.29; $^1H$ NMR ($CDCl_3$) δ8.54, 8.51 (2d, total 1H), 7.62–7.53 (1H,m), 5.22, 5.13 (total 1H, 2dd), 3.75, 3.73 (total 3H, 2s), 2.82, 2.73 (total 3H,2s).

EXAMPLE 81

(2S)-[[2-Pyridin-2-ylethyl(methyl)aminocarbonyl]oxy]-3-phenylpropionic Acid.

Using the procedure of Example 47 with the resultant ester of Example 80 gave the desired product. $^1H$ NMR ($CDCl_3$) δ8.50–8.60 (1H,m), 7.65–7.80 (1H,m), 2.83, 2.68 (total 3H,2s).

EXAMPLE 82

Benzyl
(2R)-2-Benzyl-3-[[2-pyridin-2-ylethyl(methyl)amino]-carbonylamino]propionate The resultant product from Example 23 (1.0 mmol), diphenylphosphorylazide (1.0 mmol) and triethylamine (1.0 mmol) in benzene (5 mL) were heated at reflux for 3–5 h. The mixture was cooled to 0° C. and treated with 2-(2-methylaminoethyl)pyridine (1.0 mmol). After 1 h the mixture was poured into ethyl acetate, washed with saturated $NaHCO_3$ solution and brine, dried over $Na_2$-$SO_4$ and evaporated. Chromatography of the residue on silica gel with ethyl acetate in hexane afforded the desired product.

EXAMPLE 83

(2R)-2-Benzyl-3-[[2-pyridin-2-ylethyl(methyl)amino]-carbonylamino]propionic Acid.

Using the procedure of Example 25 with the resultant compound from Example 82 gave the desired product.

EXAMPLE 84

Ethyl hydrogen (α,α-dimethylbenzyl)malonate.

Diethyl(α,α-dimethylbenzyl)malonate was prepared by the conjugate addition of phenyl magnesium bromide to diethyl isopropylidenemalonate as described by C. Holmberg [Liebigs Ann. Chem. 748 (1981)]. A solution of this diester (42.1 g, 0.15 mmol) in ethanol (100 ml) was treated by dropwise addition with a solution of potassium hydroxide (8.48 g, 0.13 mmol) in 100 ml of ethanol. After heating at 90° C. for 1 h and at 50° C. for 20 h, the reaction mixture was evaporated on the rotary evaporator to a residue. The residue was diluted with water and extracted with ether to remove unreacted starting material. The aqueous phase was cooled to 5° C., acidified to pH 3 with 6N HCl, and extracted with methylene chloride. The organic layer was washed with brine solution and dried over magnesium sulfate. Evaporation of the solvent gave 27.3 g (84%) of liquid product. $^1$H NMR (CDCl$_3$): δ1.05 (t,3H), 1.6 (s,6H), 3.78 (s,1H), 3.96 (m,2H), 7.2–7.4 (m,5H).

EXAMPLE 85

Ethyl (2R,S)-[[[2-Pyridin-2-ylethyl(methyl)amino]carbonyl]amino]-3,3-dimethyl-3-phenylpropionate.

Using the procedure of Example 82 with the resultant acid from Example 84 gave the desired product.

EXAMPLE 86

(2R,S)-[[[2-Pyridin-2-ylethyl(methyl)amino]carbonyl]amino]-3,3-dimethyl-3-phenylpropionic Acid.

Using the procedure of Example 47 with the resultant compound from Example 85 gave the desired product.

EXAMPLE 87

[2-Pyridin-2-ylethyl(methyl)amino]sulfonyl Chloride Hydrochloride.

2-(2-Methylaminoethyl)pyridine (10 mmol) was treated with excess HCl in ethanol. The mixture was evaporated and the residue was chased several times with ether and dried under high vacuum. The resulting dihydrochloride was treated with SO$_2$Cl$_2$ (30 mmol) in acetonitrile (15 mL). The mixture was heated at reflux for 24 h, cooled and filtered and the resulting solid was used with no further purification.

EXAMPLE 88

[2-Pyridin-2-ylethyl(methyl)amino]sulfonyl-(O-benzyl)threonine Methyl Ester.

To the resulting compound from Example 87 (1 mmol) and (O-benzyl)threonine methyl ester (1 mmol) in CH$_2$Cl$_2$ was added triethylamine (2.0 mmol). After 1 h the product was isolated as described in Example 80.

EXAMPLE 89

[2-Pyridin-2-ylethyl(methyl)amino]sulfonyl-(O-benzyl)threonine.

Using the procedure of Example 47 with the resultant compound of Example 88 gave the desired product.

EXAMPLE 90

(2R)-2-Benzyl-3-[(2-pyrazol-1-ylethyl)methylaminocarbonyl]propionic Acid Amide of (O-benzyl)threonine Methyl Ester The resultant product from Example 59 was coupled to (0-benzyl)threonine methyl ester using the carbodiimide procedure of Example 8.

EXAMPLE 91

(2R)-2-Benzyl-3-[(2-pyrazol-1-ylethyl)methylaminocarbonyl]propionic Acid Amide of (O-benzyl)threonine Using the procedure of Example 47 with the resultant compound from Example 90 gave the desired product.

EXAMPLE 92

(2R,4R,5S)-2-(4-Pentenyl)-4-hydroxy-5-tertbutyloxycarbonylamino-6-phenylhexanoic Acid Amide of (2S,3R,4S)-2-Amino-1-cyclohexyl-3,4-dihydroxy-6-methylheptane.

Using the procedure of Evans et al. (J. Org. Chem. 1985, 50, 4615) with the resultant compound from Example 1 and (3R,5R,1'S)-5-(1-(t-butyloxycarbonylamino)-2-phenethyl)-3-(4-pentenyl) dihydrofuran-2-(3H)-one (D. J. Kempf, J. Org. Chem. 1986, 51, 3921) gave the desired product.

EXAMPLE 93

(2R,4R,5S)-2-(4-Pentenyl)-4-hydroxy-5-[2-pyridin-2-ylethyl(methyl)amino]sulfonylamino-6-phenylhexanoic Acid Amide of (2S,3R,4S)-2-Amino-1-cyclohexyl-3,4-dihydroxy-6-methylheptane.

The resultant product from Example 92 was deprotected as described in Example 13 and coupled to the resultant compound from Example 87 as described in Example 88 to give the desired product.

EXAMPLE 94

(2R)-2-Benzyl-3-(4-trifluoroethylpiperazin-1-ylcarbonyl)propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 25 gave the desired product as a powder, m.p. 77°–83° C. TLC (10% methanol/90% chloroform) R$_f$=0.56.
Anal (C$_{37}$H$_{54}$N$_5$O$_5$F$_3$S.0.25 H$_2$O)
Calcd: C, 59.86; H, 7.40; N, 9.43.
Found: C, 59.72; H, 7.24; N, 9.30.

EXAMPLE 95

(2R)-2-Benzyl-5-morpholin-4-yl-4-oxopentanoyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 43 gave the desired product as a powder, m.p. 68°–84° C. TLC (10% methanol/90% chloroform) R$_f$=0.55.
Anal (C$_{36}$H$_{54}$N$_4$O$_6$S.0.25 H$_2$O)
Calcd: C, 64.02; H, 8.13; N, 8.30.
Found: C, 63.85; H, 8.00; N, 8.28.

EXAMPLE 96

(2R)-2-Benzyl-3-[(2-morpholin-4-ylethyl)methylaminocarbonyl]propionyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 53 gave the desired product as a powder, m.p. 115°–126° C. TLC (15% methanol/85% chloroform) R$_f$=0.49.
Anal (C$_{38}$H$_{59}$N$_5$O$_6$S.0.5 H$_2$O)
Calcd: C, 63.13; H, 8.36; N, 9.69.
Found: C, 63.50; H, 8.42; N, 9.45.

EXAMPLE 97

(2R)-2-Benzyl-3-thiazol-4-ylpropionyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 36 gave the desired product as a powder, m.p. 80°–85° C. TLC (10% methanol/90% chloroform) R$_f$=0.49.
Anal (C$_{33}$H$_{46}$N$_4$O$_4$S$_2$)
Calcd: C, 63.23; H, 7.40; N, 8.94.
Found: C, 62.84; H, 7.40; N, 8.85.

EXAMPLE 98

(2R)-2-Benzyl-5-tert-butylsulfonyl-4-oxopentanoyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 41 gave the desired product as a powder, m.p. 84°–86° C. TLC (10% methanol/90% chloroform) R$_f$=0.54.
Anal (C$_{36}$H$_{55}$N$_3$O$_7$S$_2$.0.5 H$_2$O)
Calcd: C, 60.48; H, 7.89; N, 5.88.
Found: C, 60.37; H, 7.78; N, 5.89.

EXAMPLE 99

(2R)-2-Benzyl-5-tert-butylsulfinyl-4-oxopentanoyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 40 gave the desired product as a powder, m.p. 85°–90° C. TLC (5% methanol/95% chloroform) R$_f$=0.25.
Anal (C$_{36}$H$_{55}$N$_3$O$_6$S$_2$.0.5 H$_2$O)
Calcd: C, 61.88; H, 8.07; N, 6.01.
Found: C, 61.66; H, 7.97; N, 5.90.

EXAMPLE 100

(2R)-2-Benzyl-3-(N-methoxy-N-methylamino)propionyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 48 gave, after diastereomer separation on silica gel, the desired product as a powder, m.p. 125°–128° C. TLC (ethyl acetate) R$_f$=0.28.
Anal (C$_{32}$H$_{50}$N$_4$O$_5$S)
Calcd: C, 63.76; H, 8.36; N, 9.29.
Found: C, 63.57; H, 8.41; N, 9.05.

EXAMPLE 101

(2R)-2-Benzyl-3-pyrazol-1-ylpropionyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 47 gave, after diastereomer separation on silica gel, the desired product as a powder, m.p. 85–92° C. TLC (ethyl acetate) R$_f$=0.28.
Anal (C$_{33}$H$_{47}$N$_5$O$_4$S.0.5 H$_2$O)
Calcd: C, 64.05; H, 7.82; N, 11.32.
Found: C, 64.00; H, 7.62; N, 11.14.

EXAMPLE 102

(2R)-2-Benzyl-3-imidazol-1-ylpropionyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 50 gave, after diastereomer separation on silica gel, the desired product as a powder, m.p. 77°–85° C. TLC (10% methanol/90% chloroform) R$_f$=0.30.
Anal (C$_{33}$H$_{47}$N$_5$O$_4$S.0.25 H$_2$O)
Calcd: C, 64.52; H, 7.79; N, 11.40.
Found: C, 64.36; H, 7.74; N, 11.29.

EXAMPLE 103

(2R)-2-Benzyl-3-(2-methylimino-3-methyl-2,3-dihydrothiazol-4-yl)propionyl-L-(4-thiazolyl) Ala Amide of
(2S,3R,4S)-2-Amino-1-cyclohexyl-3,4-dihydroxy-6-methylheptane Using the coupling procedure of Example 8 with the resultant compounds from Example 7 and Example 74 gave the desired product as a powder, m.p. 94°–98° C. TLC (10% methanol/90% chloroform) R$_f$=0.15.
Anal (C$_{35}$H$_{51}$N$_5$O$_4$S$_2$.0.5 H$_2$O)
Calcd: C, 61.92; H, 7.72; N, 10.31.
Found: C, 61.83; H, 7.68; N, 10.00.

EXAMPLE 104

(2R)-2-Benzyl-3-(2-dimethylaminothiazol-4-yl)propionyl-L-(4-thiazolyl)Ala Amide of
(2S,3R,4S)-2-Amino-1-cyclohexyl-3,4-dihydroxy-6-methylheptane Using the coupling procedure of Example 8 with the resultant compounds from Example 7 and Example 72 gave the desired product as a powder, m.p. 133°–138° C. TLC (10% methanol/90% chloroform) R$_f$=0.56.
Anal (C$_{35}$H$_{51}$N$_5$O$_4$S$_2$.0.25 H$_2$O)
Calcd: C, 62.33; H, 7.70; N, 10.38.
Found: C, 62.34; H, 7.64; N, 10.31.

EXAMPLE 105

(2R)-2-Benzyl-3-(5,6-dihydroimidazo[2,1-b]thiazol-3-yl)propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 76 gave the desired product as a powder, m.p. 117°-121° C. TLC (10% methanol/90% chloroform) $R_f=0.11$.
Anal ($C_{35}H_{49}N_5O_4S_2.0.5 H_2O$)
Calcd: C, 62.10; H, 7.44; N, 10.35.
Found: C, 62.02; H, 7.49; N, 10.20.

EXAMPLE 106

(2R)-2-Benzyl-3-[(2-pyrazol-1-ylethyl)methylaminocarbonyl]propionyl-L-(2-thienyl)Ala Amide of (2S,3R,4S)-2-Amino-1-cyclohexyl-3,4-dihydroxy-6-methylheptane Using the coupling procedure of Example 8 with the resultant compounds from Example 15 and Example 59 gave the desired product as a powder, m.p. 70°-77° C. TLC (10% methanol/90% chloroform) $R_f=0.58$.
Anal ($C_{38}H_{55}N_5O_5S.0.5 H_2O$)
Calcd: C, 64.93; H, 8.03; N, 9.96.
Found: C, 64.73; H, 7.85; N, 9.80.

EXAMPLE 107

(2R)-2-Benzyl-3-[(2-pyrazol-1-ylethyl)methylaminocarbonyl]propionyl-L-(1-imidazolyl)Ala Amide of (2S,3R,4S)-2-Amino-1-cyclohexyl-3,4-dihydroxy-6-methylheptane Using the coupling procedure of Example 8 with the resultant compounds from Example 14 and Example 59 gave the desired product as a powder, m.p. 85°-90° C. TLC (10% methanol/90% chloroform) $R_f=0.28$.
Anal ($C_{37}H_{55}N_7O_5.0.75 H_2O$)
Calcd: C, 64.28; H, 8.24; N, 14.18.
Found: C, 64.68; H, 8.27; N, 13.52.

EXAMPLE 108

(2R)-2-Benzyl-3-(1-methylazetidin-3-ylsulfonyl)propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 70 gave, after diastereomer separation on silica gel, the desired product as a powder, m.p. 153°-155° C. TLC (10% methanol/90% chloroform) $R_f=0.29$.
Anal ($C_{34}H_{52}N_4O_6S_2.0.25 H_2O$)
Calcd: C, 59.93; H, 7.77; N, 8.22.
Found: C, 59.86; H, 7.60; N, 8.15.

EXAMPLE 109

(2R)-2-Benzyl-3-[[2-pyridin-2-ylethyl(methyl)amino]sulfonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 64 gave, after diastereomer separation on silica gel, the desired product as a powder, m.p. 76°-81° C. TLC (10% methanol/90% chloroform) $R_f=0.45$.
Anal ($C_{38}H_{55}N_5O_6S_2.1.25 H_2O$)
Calcd: C, 5g.70; H, 7.58; N, 9.16.
Found: C, 59.50; H, 7.31; N, 9.03.

EXAMPLE 110

(2RS)-2-Benzyl-3-(1-methylazetidin-3-ylsulfonyl)propionyl-Nle Amide of (2S,3R,4S)-2-Amino-1-cyclohexyl-3,4-dihydroxy-6-methylheptane Using the coupling procedure of Example 8 with the resultant compounds from Example 16 and Example 70 gave the desired product as a powder, m.p. 103°-110° C. TLC (10% methanol/90% chloroform) $R_f=0.39, 0.42$.
Anal ($C_{34}H_{57}N_3O_6S.1.25 H_2O$)
Calcd: C, 62.02; H, 9.11; N, 6.38.
Found: C, 62.01; H, 8.90; N, 6.14.

EXAMPLE 111

(2R)-2-Benzyl-3-[(2-pyrazol-1-ylethyl)methylaminocarbonyl]propionyl-L-(4-Thiazolyl)Ala Amide of (4S,5R,6S)-6-Amino-4,5-dihydroxy-2,8-dimethylnonane Using the coupling procedure of Example 8 with the resultant compounds from Example 19 and Example 59 gave the desired product as a powder, m.p. 70°-76° C. TLC (10% methanol/90% chloroform) $R_f=0.44$.

EXAMPLE 112

(2R)-2-Benzyl-3-[(2-pyrazol-1-ylethyl)methylaminocarbonyl]propionyl-L-(4-Thiazolyl)Ala Amide of (2S,3R,4S)-2-Amino-1-cyclohexyl-3,4-dihydroxyhexane Using the coupling procedure of Example 8 with the resultant compounds from Example 18 and Example 59 gave the desired product as a powder, m.p. 68°-73° C. TLC (10% methanol/90% chloroform) $R_f=0.41$.
Anal ($C_{35}H_{50}N_6O_5S.0.5 H_2O$)
Calcd: C, 62.20; H, 7.61; N, 12.43.
Found: C, 61.89; H, 7.09; N, 12.09.

EXAMPLE 113

(2S)-2-(4-Morpholinyl)-3-phenylpropionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 33 gave the desired product as a powder, m.p. 140°-144° C. TLC (15% methanol/85% chloroform) $R_f=0.63$.
Anal ($C_{33}H_{50}N_4O_5S$)
Calcd: C, 64.46; H, 8.20; N, 9.11.
Found: C, 64.40; H, 8.34; N, 8 81.

EXAMPLE 114

(2R)-2-Benzyl-3-(2-pyridin-2-ylethyl)methylaminocarbonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 29 gave the desired product as a powder, m.p. 115°-121° C. TLC (15% methanol/85% chloroform) $R_f=0.64$.
Anal ($C_{39}H_{55}N_5O_5S.0.5 H_2O$)
Calcd: C, 65.51; H, 7.75; N, 9.80.
Found: C, 65.78; H, 7.93; N, 9.82.

EXAMPLE 115

[2-Pyridin-2-ylethyl(methyl)amino]carbonyl(O-methyl)pyrosine-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 79 gave the desired product as a powder, m.p. 120°–126° C. TLC (15% methanol/85% chloroform) $R_f$=0.62.
Anal ($C_{39}H_{56}N_6O_6S.0.5 H_2O$)
Calcd: C, 62.79; H, 7.70; N, 11.27.
Found: C, 63.07; H, 7.72; N, 11.01.

EXAMPLE 116

(2R)-2-Benzyl-3-[2-(4-methyloioerazin-1-ylethyl)methylaminocarbonyl]propionyl-L-(4-thiazolyl) Ala Amide of (2S,3R,4S)-2-Amino-1-cyclohexyl-3,4-dihydroxy-6-methylheptane Using the coupling procedure of Example 8 with the resultant compounds from Example 7 and Example 57 gave the desired product as a powder, m.p. 122°–130° C. TLC (15% methanol/85% chloroform) $R_f$=0.27.
Anal ($C_{39}H_{62}N_6O_5S.0.5 H_2O$)
Calcd: C, 63.64; H, 8.63; N, 11.42.
Found: C, 63.69; H, 8.58; N, 11.31.

EXAMPLE 117

(2R)-2-Benzyl-3-[(2-imidazol-1-ylethyl)methylaminocarbonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 55 gave the desired product as a powder, m.p. 155°–161° C. TLC (15% methanol/85% chloroform) $R_f$=0.35.
Anal ($C_{37}H_{54}N_6O_5S.2 H_2O$)
Calcd: C, 60.80; H, 8.00; N, 11.50.
Found: C, 60.91; H, 7.71; N, 11.23.

EXAMPLE 118

(2R)-2-Benzyl-3-[(2-pyrazol-1-ylethyl)methylaminocarbonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 59 gave the desired product as a powder, m.p. 122°–133° C. TLC (15% methanol/85% chloroform) $R_f$=0.59.
Anal ($C_{37}H_{54}N_6O_5S$)
Calcd: C, 63.95; H, 7.83; N, 12.09.
Found: C, 63.02; H, 7.76; N, 11.80.

EXAMPLE 119

(2R)-2-Benzyl-3-[(2-pyridin-2-ylethyl)methylaminocarbonyl]propionyl-L-(1-pyrazolyl)Ala Amide of (2S,3R,4S)-2-Amino-1-cyclohexyl-3,4-dihydroxy-6-methylheptane Using the coupling procedure of Example 8 with the resultant compounds from Example 13 and Example 29 gave the desired product as a powder, m.p. 132°–138° C. TLC (15% methanol/85% chloroform) $R_f$=0.59.
Anal ($C_{39}H_{56}N_6O_5.0.5 H_2O$)
Calcd: C, 67.12; H, 8.23; N, 12.04.
Found: C, 67.06; H, 8.11; N, 11.88.

EXAMPLE 120

(2R)-2-Benzyl-3-[(2-imidazol-1-ylethyl)methylaminocarbonyl]propionyl-L-(1-pyrazolyl)Ala Amide of (2S,3R,4S)-2-Amino-1-cyclohexyl-3,4-dihydroxy-6-methylheptane Using the coupling procedure of Example 8 with the resultant compounds from Example 13 and Example 55 gave the desired product as a powder, m p. 105°–110° C. TLC (15% methanol/85% chloroform) $R_f$=0.45.
Anal ($C_{37}H_{55}N_7O_5.0.5 H_2O$)
Calcd: C, 64.70; H, 8.22; N, 14.27.
Found: C, 64.41; H, 8.06; N, 14.15.

EXAMPLE 121

(2R)-2-Benzyl-3-[(2-pyrazol-1-ylethyl)methylaminocarbonyl]propionyl-Nle Amide of (2S,3R,4S)-2-Amino-1-cyclohexyl-3,4-dihydroxy-6-methylheptane Using the coupling procedure of Example 8 with the resultant compounds from Example 16 and Example 59 gave the desired product as a powder, m.p. 105°–110° C. TLC (15% methanol/85% chloroform) $R_f$=0.62.
Anal ($C_{37}H_{59}N_5O_5$)
Calcd: C, 67.96; H, 9.09; N, 10.71.
Found: C, 67.85; H, 9.10; N, 10.48.

EXAMPLE 122

(2R)-2-Benzyl-3-[(2-pyridin-2-ylethyl)methylaminocarbonyl]propionyl-Nle Amide of (2S,3R,4S)-2-Amino-1-cyclohexyl-3,4-dihydroxy-6-methylheptane Using the coupling procedure of Example 8 with the resultant compounds from Example 16 and Example 29 gave the desired product as a powder, m.p. 105°–110° C. TLC (15% methanol/85% chloroform) $R_f$=0.60.
Anal ($C_{39}H_{60}N_4O_5$)
Calcd: C, 70.45; H, 9.09; N, 8.43.
Found: C, 70.14; H, 9.15; N, 8.26.

EXAMPLE 123

(2R)-2-Benzyl-3-[(2-imidazol-1-ylethyl)methylaminocarbonyl]propionyl-Nle Amide of (2S,3R,4S)-2-Amino-1-cyclohexyl-3,4-dihydroxy-6-methylheptane Using the coupling procedure of Example 8 with the resultant compounds from Example 16 and Example 55 gave the desired product as a powder, m.p. 130°–140° C. TLC (15% methanol/85% chloroform) $R_f$=0.41.
Anal ($C_{37}H_{59}N_5O_5$)
Calcd: C, 67.96; H, 9.09; N, 10.71.
Found: C, 68.03; H, 9.18; N, 10.48.

EXAMPLE 124

(2R)-2-Benzyl-3-[(N-pyridin-4-yl)methylaminocarbonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 31 gave the desired product, m.p. 85°–92° C.

EXAMPLE 125

(2R)-2-Benzyl-3-[(4-cyclopropylpiperazin-1-yl)carbonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7 and Example 27 gave the desired product as a powder, m.p. 78°–83° C.
Anal ($C_{38}H_{57}N_5O_5S.0.6\ H_2O$)
Calcd: C, 64.58; H, 8.13; N, 9.91.
Found: C, 64.64; H, 8.16; N, 9.97.

EXAMPLE 126

(2S)-[[2-Pyridin-2-ylethyl(methyl)aminocarbonyl]oxy]-3-phenylpropionyl-L-(1-pyrazolyl)Ala Amide of (2S,3R,4S)-2-Amino-1-cyclohexyl-3,4-dihydroxy-6-methylheptane Using the coupling procedure of Example 8 with the resultant compounds from Example 13 and Example 81 gave the desired product as a powder, m.p. 165°–168° C. TLC (10% methanol/90% chloroform) $R_f=0.60$.
Anal ($C_{38}H_{54}N_6O_6.0.5\ H_2O$)
Calcd: C, 65.21; H, 7.92; N, 12.01.
Found: C, 65.06; H, 7.80; N, 12.02.

EXAMPLE 127

(2R)-2-Benzyl-3-[2-pyridin-2-ylethyl(methyl)amino]carbonylamino]propionyl-L-(1-pyrazolyl)Ala Amide of (2S,3R,4S)-2-Amino-1-cyclohexyl-3,4-dihydroxy-6-methylheptane Using the coupling procedure of Example 8 with the resultant compounds from Example 13 and Example 83 gave the desired product.

EXAMPLE 128

(2R)-[[[2-Pyridin-2-ylethyl(methyl)amino]carbonyl]amino]-3,3-dimethyl-3-phenylpropionyl-Met Amide of (2S,3R,4S)-2-Amino-1-cyclohexyl-3,4-dihydroxy-6-methylheptane Using the coupling procedure of Example 8 with the resultant compounds from Example 17 and Example 86 gave the desired product after diastereomer separation.

EXAMPLE 129

[2-Pyridin-2-ylethyl(methyl)amino]sulfonyl-(O-benzyl)threonine-Nle Amide of (2S,3R,4S)-2-Amino-1-cyclohexyl-3,4-dihydroxy-6-methylheptane Using the coupling procedure of Example 8 with the resultant compounds from Example 16 and Example 89 gave the desired product.

EXAMPLE 130

(2R)-2-Benzyl-3-[(2-pyrazol-1-ylethyl)methylaminocarbonyl]propionyl-(O-benzyl)threonine Amide of (2S,3R,4S)-2-Amino-1-cyclohexyl-3,4-dihydroxy-6-methylheptane Using the coupling procedure of Example 8 with the resultant compounds from Example 1 and Example 91 gave the desired product.

EXAMPLE 131

L-Boc-(N-α-methyl)-(1-pyrazolyl)alanine

To the resultant compound from Example 2 (1.042 g, 4.082 mmol) in tetrahydrofuran (12 mL) at 0° C. was added methyl iodide (2.00 mL, 32.1 mmol) followed by sodium hydride (520 mg. 13.0 mmol, 60% in oil). After 18 h at ambient temperature the mixture was quenched with water, concentrated, diluted with water, and washed with ether. The ether was extracted with saturated $NaHCO_3$ solution and the combined aqueous layers were acidified to pH 3 with 0.5M $H_3PO_4$ and extracted twice with ethyl acetate which was dried over $Na_2SO_4$ and evaporated to yield 1.009 g (92%) of a foam. TLC (20% methanol/1% acetic acid/79% chloroform) $R_f=0.52$; $^1H$ NMR ($CDCl_3$) δ7.55–7.60 (1H,m), 7.34, 7.37 (total 1H,2d), 6.24–6.30 (1H,m), 4.43–4.90 (3H,m), 2.69,2.66 (total 3H,2s), 1.45,1.44 (total 9H,2s).

EXAMPLE 132

L-Boc-(N-α-methyl)-(1-pyrazolyl)alanine Amide of (2S,3R,4S)-2-Amino-1-cyclohexyl-3,4-dihydroxy-6-methylheptane Using the procedure of Example 8 and replacing the resultant compound from Example 2 with the resultant compound from Example 131 gave the desired product as a foam. TLC (10% methanol/90% chloroform) $R_f=0.61$.

EXAMPLE 133

H-(N-α-methyl)-(1-pyrazolyl)alanine Amide of (2S,3R,4S)-2-Amino-1cyclohexyl-3,4-dihydroxy-6-methylheptane Using the procedure of Example 13 with the resultant compound from Example 132 gave the desired product as a solid, m.p. 114°–117° C. TLC (10% methanol/90% chloroform) $R_f=0.45$.
Anal ($C_{21}H_{38}N_4O_3$)
Calcd: C, 63.g3; H, 9.71; N, 14.20.
Found: C, 63.88; H, 9.67; N, 13.79.

EXAMPLE 134

(2R)-2-Benzyl-3-[(2-pyridin-2-ylethyl)methylaminocarbonyl]propionyl-(N-α-methyl)-(1-pyrazolyl) alanine Amide of (2S,3R,4S)-2-Amino-1-cyclohexyl-3,4-dihydroxy-6-methylheptane To the resultant compounds from Example 29 (48.6 mg, 0.149 mmol) and Example 133 (50.3 mg, 0.127 mmol) in methylene chloride (1 mL) at 0° C. was added triethyl amine (0.050 mL, 0.36 mmol) followed by Bis(2-oxo-3-oxazolidinyl)-phosphinic chloride (39.0 mg, 0.153 mmol). After 15 h at 0° C. the mixture was diluted with ethyl acetate, washed with saturated $NaHCO_3$ solution, water and brine, then dried over $Na_2SO_4$ and evaporated. Chromatography of the residue on silica gel with 1.5% methanol in chloroform afforded 79.9 mg (89%) of the desired product as a foam. TLC (5% methanol/95% chloroform) $R_f=0.48$.
Anal ($C_{40}H_{58}N_6O_5.0.5\ H_2O$)
Calcd: C, 6?.48; H, 8.35; N, 11.80.
Found: C, 67.55; H, 8.30; N, 11.60.

EXAMPLE 135

N-Methyl-N-2-[(2-pyridylethyl)]-3(S)-acetoxy-2(R)benzylsuccinamide

To a solution of 1.1 g (3.8 mmol) of diethyl (2R,3S)-2-benzyl-3-hydroxy succinate, prepared according to the procedure of D. Seebach, Org. Syn., 63, 109, in 16 mL of tetrahydrofuran, cooled in an ice-water bath was added 440 mg (10.4 mmol) of lithium hydroxide monohydrate in 16 mL water. The bath was removed and the reaction stirred for 18 h. The reaction mixtured was acidified with concentrated HCl until pH 4 and the solvents rempyed under high vacuum to give a white solid. The crude diacid was warmed to 50° C. in 8 mL of 1:1 acetic anhydride/acetyl chloride for 3 h. Excess acetic anhydride/acetyl chloride was rempyed under high vacuum. The residue is dissolved in 5 mL of methylene chloride, cooled in an ice-water bath and 0.51 g (3.8 mmol) of 2-(2-methylamminoethyl)pyridine is added. The reaction is stirred for 1 h and the solvents rempyed under high vacuum. The crude acid is used without further purification.

EXAMPLE 136

(2R, 3S)-3-Acetoxy-2-benzyl-3-[2-(2-pyridylethyl)methylaminocarbonyl]propionyl-L-(4-thiazolyl)Ala Amide of (2S,3R,4S)-2-Amino 1-cyclohexyl-3,4-dihydroxy-6-methylheptane.

Using the coupling procedure of Example 8 with the resultant compounds from Example 135 and Example 7 gives the desired product.

EXAMPLE 137

Ethyl (2S, 3R) 2-Benzyl-3-[2-(2-pyridylethyl)methylaminocarbonyl]-3-hydroxypropionate To a solution of 400 mg (1.42 mmol) of diethyl (2S 3R)-3-benzyl-2-hydroxypropionate in 2 mL of tetrahydrofuran cooled in an ice-water bath was added a 1 mL water solution of 55 mg (1.42 mmol) of lithium hydroxide monohydrate. The bath was rempyed and the reaction stirred for one hour. The pH is adjusted to pH 3-4 with aqueous saturated potassium hydrogen sulfate and the product acid was extracted with methylene chloride. The crude monoacid is dissolved into 2 mL of methylene chloride and 0.38 g (2.8 mmol) of 2-(2-methylaminoethyl)pyridine, 0.2 mL ethyl diisopropyl amine and 0.2 mL diethylphosphonocyanide is added. The reaction mixture is stirred for 18 h at room temperature and concentrated under high vacuum. The crude residue is purified by flash chromatography to give the desired product.

EXAMPLE 138

(2S, 3R)-Benzyl-3-[2-(2-pyrdylethyl)methylaminocarbonyl]-3-hydroxypropionic Acid Lithium Salt A solution of 0.16 g (0.45 mmol) of ester from Example 137 in 3 mL of tetrahydrofuran is treated with mg (0.5 mmol) of lithium hydroxide monohydrate in 3 mL of water. The reaction is stirred at room temperature for 18 h. The solvents are rempyed under high vacuum to give a solid lithium salt which is used without further purification.

EXAMPLE 139

(2R, 3S)-2-benzyl-3-hydroxy-3-[2-(2-pyridylethyl)methylaminocarbonyl]propionyl-L-(4-thiazolyl)Ala Amide of (2S,3R,4S)-2-Amino 1-cyclohexyl-3,4-dihydroxy-6-methylheptane.

The resulting acid salt from Example 138, 1-HOBT (48 mg, 0.45 mmol), 4-methylmorpholine(135 mg, 0.45 mmol) and the resultanting compound from Example 7 are dissolved in mL of DMF, using the procedure of Example 8, to give the title compound.

EXAMPLE 140

(2R)-2-Benzyl-3-[(2-morpholin-4-ylethyl)methylaminocarbonyl]propionyl-L-(1-pyrazolyl)Ala Amide of (2S,3R,4S)-2-Amino-1-cyclohexyl-3,4-dihydroxy-6-methylheptane.

Using the coupling procedure of Example 8 with the resultant compounds from Example 13 and Example 53 gave the desired product as a powder, m.p. 135°-142° C. TLC (15% methanol/85% chloroform) $R_f=0.58$.

Anal ($C_{38}H_{60}N_6O_6.0.5\ H_2O$)

Calcd: C, 64.65; H, 8.71; N, 11.90.

Found: C, 64.81; H, 8.57; N, 11.76.

EXAMPLE 141

(2R)-2-Benzyl-3-[(2-pyridin-2-ylethyl)methylaminocarbonyl]propionyl-L-(1-imidazolyl)Ala Amide of (2S,3R,4S)-2-Amino-1-cyclohexyl-3,4-dihydroxy-6-methylheptane Using the coupling procedure of Example 8 with the resultant compounds from Example 14 and Example 29 gave the desired product as a powder, m.p. 142°-147° C. TLC (15% methanol/85% chloroform) $R_f=0.43$.

Anal ($C_{39}H_{56}N_6O_5.0.5\ H_2O$)

Calcd: C, 67.12; H, 8.23; N, 12.04.

Found: C, 67.12; H, 8.16; N, 11.73.

EXAMPLE 142

(2R)-2-Benzyl-3-[(2-pyrazol-1-ylethyl)methylaminocarbonyl]propionyl-L-(1-pyrazolyl)Ala Amide of (2S,3R,4S)-2-Amino-1-cyclohexyl-3,4-dihydroxy-6-methylheptane Using the coupling procedure of Example 8 with the resultant compounds from Example 13 and Example 59 gave the desired product as a powder, m.p. 135°-140° C. TLC (15% methanol/85% chloroform) $R_f=0.62$.

Anal ($C_{37}H_{55}N_7O_5.0.5\ H_2O$)

Calcd: C, 64.70; H, 8.22; N, 14.27.

Found: C, 64.69; H, 8.14; N, 14.24.

EXAMPLE 143

Benzyl (2R)-2-Benzyl-3-[(2-indol-3-ylethyl)methylaminocarbonyl]propionate.

Using the procedure of Example 24 and replacing 1trifluoroethylpiperazine with N-methyltryptamine gave the desired product. TLC (ethyl acetate) $R_f=0.55$; $^1$H NMR (CDCl$_3$) δ5.16, 5.12, 5.08, 5.01 (4d, total 2H), 2.93, 2.81 (2s, total 3H).

EXAMPLE 144

(2R)-2-Benzyl-3-[(2-indol-3-ylethyl)methylaminocarbonyl]propionic Acid

Prepared from the resultant compound of Example 143 according to the procedure of Example 25, m.p. 90°-100° C. $^1$H NMR (CDCl$_3$) δ2.93, 2.81 (2s, total 3H).

EXAMPLE 145

Benzyl (2R)-2-Benzyl-3-[(2-pyridin-4-ylethyl)methylaminocarbonyl]propionate.

Using the procedure of Example 24 and replacing 1-trifluoroethylpiperazine with 4-(2-methylaminoethyl)pyridine gave the desired product. TLC (15% methanol/85% chloroform) $R_f=0.58$; $^1$H NMR (CDCl$_3$) $\delta$8.50 (br s, 2H), 7.37–6.96 (m, 12H), 5.20–5.02 (m, 2H), 2.88, 2.82 (2s, total 3H), 2.30, 2.14 (2dd, total 1H).

EXAMPLE 146

(2R)-2-Benzyl-3-[(2-pyridin-4-ylethyl)methylaminocarbonyl]propionic Acid

Prepared from the resultant compound of Example 145 according to the procedure of Example 25. $^1$H NMR (CDCl$_3$) $\delta$8.55–8.41 (m, 2H), 7.33–6.93 (m, 7H), 2.87, 2.76 (2s, total 3H).

EXAMPLE 147

Benzyl (2R)-2-Benzyl-3-[(2-pyrrolidin-1-ylethyl)methylaminocarbonyl]propionate.

Using the procedure of Example 52 and replacing morpholine with pyrrolidine gave the desired product. TLC (15% methanol/85% chloroform) $R_f=0.32$; $^1$H NMR (CDCl$_3$) $\delta$7.38–7.10 (m, 10H), 5.165, 5.160 (2d, total 1H), 5.05 (d, 1H), 3.96, 3.89 (2s, total 3H), 1.86–1.70 (m, 4H).

EXAMPLE 148

(2R)-2-Benzyl-3-[(2-pyrrolidin-1-ylethyl)methylaminocarbonyl]propionic Acid ylethyl)methylaminocarbonyl propionic Acid Prepared from the resultant compound of Example 147 according to the procedure of Example 25. $^1$H NMR (CDCl$_3$) 7.30–7.13 (m, 5H), 3.02, 2.92 (2s, total 3H), 1.98–1.90, 1.82–1.45 (m, total 4H).

EXAMPLE 149

[(2-pyridin-2-ylethyl)methylaminocarbonyl]phenylalanine Benzyl Ester

To ($\alpha$-isocyanato)Phe-OBn (0.5057 g, 1.80 mmol) in methylene chloride at 0 °C. was added 2-(2-methylaminoethyl)-pyridine (0.250 mL, 1.81 mmol). After 1 h the mixture was evaporated to a pale yellow oil. TLC (ethyl acetate) $R_f=0.16$; $^1$H NMR (CDCl$_3$) $\delta$8.42 (dt, 1H), 7.58 (dt, 1H), 7.40–7.02 (m, 12H), 5,67 (br s, 1H), 5.17 (d, 1H), 5.08 (d, 1H), 4.79 (dd, 1H), 3.78–3.53 (m, 2H), 3.10 (d, 2H), 3.01 (dd, 2H), 2.79 (s, 3H).

EXAMPLE 150

[(2-pyridin-2-ylethyl)methylaminocarbonyl]phenylalanine

Prepared from the resultant compound of Example 147 according to the procedure of Example 25. $^1$H NMR (CDCl$_3$) $\delta$8.47 (dt, 1H), 7.65 (dt, 1H), 7.30–7.12 (m, 5H), 6.50 (br s, 1H), 4.42 (ddd, 1H), 2.78 (s, 3H).

EXAMPLE 151

L-(3-Pyrazolyl)alanine Amide of (2S,3R,4S)-2-Amino-1-cyclohexyl-3,4-dihydroxy-6-methylheptane Using the procedure of Example 7 and replacing Boc-L-(4-thiazolyl)Ala-OH with Boc-DL-(4-pyrazolyl)ala-OH (Hofmann et al, J. Am. Chem. Soc. 90, 6207 (1968) afforded the intermediate dl-Boc-protected compound. This material was stirred for 2 h in 4M HCl/dioxane, the solvent was evaporated and the residue was dissolved in water which was basified with K$_2$CO$_3$. The product was extracted into chloroform which was dried and evaporated. Chromatography on silica gel with methanol/chloroform mixtures afforded the desired L-isomer. $^1$H NMR (CDCl$_3$) $\delta$7.52 (d,1H), 7.35 (d,1H), 6.19 (d,1H), 4.34–4.22 (m,1H), 3.16 (dd,1H), 3.07 (dd,1H), 0.93 (d, 3H), 0.85 (d, 3H).

EXAMPLE 152

(2R)-2-Benzyl-3-[(2-indol-3-ylethyl)methylaminocarbonyl]propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7B and Example 144 gave the desired product as a powder, m.p. 160°–165° C. TLC (15% methanol/85% chloroform) $R_f=0.63$.

Anal (C$_{42}$H$_{57}$N$_5$O$_5$S.0.5 H$_2$O)
Calcd: C, 66.99; H, 7.76; N, 9.30.
Found: C, 67.37; H, 7.69; N, 9.26.

EXAMPLE 153

(2R)-2-Benzyl-3-[(2-pyrrol-1-ylethyl)methylcarbonyl]-propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7B and Example 148 gave the desired product as a powder, m.p. 110°–120° C. TLC (15% methanol/85% chloroform) $R_f=0.24$.

Anal (C$_{38}$H$_{59}$N$_5$O$_5$S.H$_2$O)
Calcd: C, 63.75; H, 8.59; N, 9.78.
Found: C, 63.99; H, 8.36; N, 9.67.

EXAMPLE 154

(2R)-2-Benzyl-3-[(2-pyridin-4-ylethyl)methylcarbonyl]-propionyl-L-(4-thiazolyl)Ala Amide of (2S,3R,4S)-2-Amino-1-cyclohexyl-3,4-dihydroxy-6-methylheptane Using the coupling procedure of Example 8 with the resultant compounds from Example 7B and Example 146 gave the desired product as a powder, m.p. 115°–125° C. TLC (15% methanol/85% chloroform) $R_f=0.57$.

Anal (C$_{39}$H$_{55}$N$_5$O$_5$S.0.5 H$_2$O)
Calcd: C, 65.52; H, 7.89; N, 9.80.
Found: C, 65.20; H, 7.85; N, 9.52.

EXAMPLE 155

(2R)-2-Benzyl-3-[(2-morpholin-4-ylethyl)methylcarbonyl]propionyl-L-(3-pyrazolyl)Ala Amide of (2S,3R,4S)-2-Amino-1-cyclohexyl-3,4-dihydroxy-6-methylheptane Using the coupling procedure of Example 8 with the resultant compounds from Example 151 and Example 53 gave the desired product as a powder, m.p. 160°–165° C. TLC (15% methanol/85% chloroform) $R_f=0.36$.

Anal ($C_{38}H_{60}N_6O_6 \cdot H_2O$)
Calcd: C, 64.65; H, 8.71; N, 11.90.
Found: C, 64.60; H, 8.63; N, 11.71.

EXAMPLE 156

[(2-pyridin-2-ylethyl)methylcarbonyl]phenylalanine-L-(N-α-methyl)-(1-pyrazolyl)alanine Amide of (2S,3R,4S)-2Amino-1-cyclohexyl-3,4-dihydroxy-6-methylheptane Using the coupling procedure of Example 134 with the resultant compounds from Example 133 and Example 150 gave the desired product as a foam. TLC (5% methanol/95% chloroform) $R_f=0.39$.

Anal ($C_{39}H_{57}N_7O_5 \cdot 0.5 H_2O$)
Calcd: C, 65.70; H, 8.20; N, 13.75.
Found: C, 65.75; H, 8.27; N, 13.54.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maeate, methanesulfonate, nicotinate, 2-naphthalenesulfonate, oxalate, pamoate, pectinate, persulfate, 3-phenyl-propionate, picrate, pivalate, propionate, succinate, tartrate, thiocyanate, tosylate, mesylate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl., and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl-substituted compound of formula I which has been acylated with a blocked or unblocked amino acid residue, a phosphate function, or a hemisuccinate residue. The amino acid esters of particular interest are glycine and lysine; however, other amino acid residues can also be used. Other esters include the compounds of formula I wherein a carboxylic acid group has been esterified to provide esters which include, but are not limited to, methyl, ethyl or benzyl esters. These esters serve as prodrugs of the compounds of the present invention and serve to increase the solubility of these substances in the gastrointestinal tract. These pro-drugs are metabolized in vivo to provide the hydroxyl-substituted compound of formula I. The preparation of the pro-drug esters is carried out by reacting a hydroxyl-substituted compound of formula I with an activated amino acyl, phosphoryl or hemisuccinyl derivative. The resulting product is then deprotected to provide the desired pro-drug ester. Prodrugs which are esters of carboxylic acid group containing compounds of formula I are prepared by methods known in the art.

The novel compounds of the present invention possess an excellent degree of activity and specificity in treating hypertension in a mammal (especially humans). The compounds of the invention are also useful for treating congestive heart failure in a mammal. The ability of the compounds of the invention to inhibit human renal renin can be demonstrated in vitro by reacting a selected compound at varied concentrations with human renal renin, free from acid proteolytic activity, and with renin substrate (human angiotensinogen) at 37 degrees C and pH of 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the results shown in table 1 were obtained.

TABLE 1

| Example | $IC_{50}$ (nM) |
|---|---|
| 94 | 0.57 |
| 95 | 0.56 |
| 96 | 0.40 |
| 97 | 0.68 |
| 98 | 0.45 |
| 99 | 0.91 |
| 100 | 1.80 |
| 101 | 0.67 |
| 102 | 0.69 |
| 103 | 0.43 |
| 104 | 0.43 |
| 105 | 1.10 |
| 106 | 0.38 |
| 107 | 0.89 |
| 108 | 0.44 |
| 109 | 0.25 |
| 110 | 2.30 |
| 111 | 0.49 |
| 112 | 0.25 |
| 113 | 0.15 |
| 114 | 0.33 |
| 115 | 0.78 |
| 116 | 0.35 |
| 117 | 0.30 |
| 118 | 0.30 |
| 119 | 0.33 |
| 120 | 0.22 |
| 121 | 0.33 |
| 122 | 0.43 |
| 123 | 0.26 |
| 124 | 0.34 |
| 125 | 0.55 |
| 134 | 1.30 |
| 140 | 0.12 |
| 141 | 0.88 |
| 142 | 0.19 |
| 152 | 0.59 |
| 153 | 0.28 |
| 154 | 0.21 |
| 155 | 0.32 |
| 156 | 1.3 |

The results shown indicate that the compounds of the invention are renin inhibitors.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present invention also relates to the use of the compounds of Formula I for treating vascular diseases, especially those vascular diseases associated with diabetes, such as diabetic nephropathy, diabetic neuropathy and diabetic retinopathy. The compounds are also useful for the treatment of renal failure. The compounds are also useful for treating psoriasis.

The compounds of the present invention are also useful for treating glaucoma or reducing and/or controlling intraocular pressure in a mammal. Compositions for this purpose are administered as topical or systemic pharmaceutical compositions. These compositions are preferably administered as topical pharmaceutical compositions suitable for ophthalmic administration, in a pharmaceutical vehicle such as pharmaceutically acceptable sterile aqueous or nonaqueous solutions, suspensions, emulsions, ointments and solid insersts.

Examples of suitable pharmaceutically acceptable vehicles for ophthalmic administration are water, propylene glycol and other pharmaceutically acceptable alcohols, sesame or peanut oil and other pharmaceutically acceptable oils, petroleum jelly, water soluble ophthalmically acceptable non-toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xanthan gum; and mixtures of these polymers. Such compositions may also contain adjuvants such as buffering, preserving, wetting, emulsifying and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositons of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositons for treating glaucoma or reducing and/or controlling intraocular pressure may be varied so as to obtain a desired therapeutic response to a particular composition. Generally, the active compound will be administered as an isotonic aqueous solution of from 0.00001 to 1.0 (w/v) percent concentration. More preferably, the active compound will be administered as an isotonic aqueous solution of from 0.00001 to 0.1 (w/v) percent concentration.

The term "controlling intraocular pressure" as used herein means the regulation, atenuation and modulation of increased intraocular tension. The term also means that the decrease, in the otherwise elevated intraocular pressure, obtained by the methods and compositions of the invention is maintained for a significant period of time as, for example, between consecutive doses of the composition of the invention.

The effect on intraocular pressure of the compounds of the invention can be determined in rabbits by using the following method.

Effects of Topically Administered Renin Inhibiting Compounds on Intraocular Pressure in Rabbits a. Method The antiglaucoma activity of the compounds is tested by measuring the effect on intraocular pressure in rabbits as described by Tinjum, Acta Ophthalmologica, 50 677 (1972). Male albino, New Zealand rabbits are placed in restraining devices and the intraocular pressure is measured with an applamatic tonometer. Exactly 0.1 ml of an isotonic saline solution containing a test compound is instilled into the conjuctival sac and the intraocular pressure is measured at 5, 15, 30, 60, 90, 120 and 180 minutes afterwards.

The present invention is also directed to the use of compounds of the formula I in combination with one or more antihypertensive agents independently selected from diuretics, adrenergic blocking agents, vasodilators, calcium channel blockers, angiotensin converting enzyme (ACE) inhibitors, potassium channel activators and other antihypertensive agents.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative antihypertensive agents include sympatholytic agents such as methyldopa, clonidine, guanabenz, reserpine and the like or a pharmaceutically acceptable salt thereof.

Combinations of a compound of formula I with one or more of the above-mentioned antihypertensive agents are useful for the treatment of hypertension or congestive heart failure.

The compound of formula I and the antihypertensive agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

In addition, the present invention is directed to the use of a compound of formula I to inhibit retroviral proteases and in particular to inhibit HIV-1 protease and HIV-2 protease. Compounds of formula I are useful for treatment or prophylaxis of diseases in mammals (especially humans) caused by retroviruses, especially acquired immune deficiency syndrome or an HIV infection.

The antiviral activity of compounds of the invention can be demonstrated using the following method.

A mixture of 0.1 ml ($4 \times 10^6$ cells/ml) of H9 cells and 0.1 ml (100 infectious units) of HIV-13B was incubated on a shaker for 2 h. The resulting culture was washed three times, resuspended into 2 ml of medium, and treated with 10 $\mu$l of the compound of the invention (5 mM in dimethylsulfoxide). The control culture was treated in an identical manner except the last step was omitted. After incubation of the culture for eight days without change of medium, an aliquot (0.1 ml) of the supernatent was withdrawn and incubated with fresh H9 cells on a shaker for 2 h. The resulting culture was washed three times, resuspended into 2 ml of medium, and incubated. Virus infectivity was determined using the Abbott HTLV-III antigen E.I.A. method (Paul, et al., J. Med. Virol., 22 357 (1987)).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

$$A-\underset{R_1}{\underset{|}{C}}(=O)-NH-\underset{R_3}{\underset{|}{C}}H-C(=O)-\underset{H}{\underset{|}{N}}-CH(OH)-CH(OH)-CH_2-CH(CH_3)-CH_3$$

(with $R_4$ substituent)

wherein

A is $R_{13}$—Q—B—wherein $R_{13}$ is (heterocyclic)amino, (heterocyclic)aminoalkyl, (heterocyclic)(alkyl)amino, (heterocyclic)(alkyl)aminoalkyl, ((heterocyclic)alkyl)amino, ((heterocyclic)alkyl)aminoalkyl, ((heterocyclic)alkyl)(alkyl)amino or ((heterocyclic)alkyl)(alkyl)aminoalkyl; Q is —C(O)—or —S(O)$_2$—; and B is —NH—, —N(loweralkyl)—, —S—, —O—, —CH$_2$—or —CH(OH)—;

$R_1$ is loweralkyl, cycloalkylalkyl, arylalkyl, aryloxyalkyl, thioaryloxyalkyl, arylaminoalkyl, aryloxy, thioaryloxy or arylamino;

$R_3$ is loweralkyl, alkenyl, alkoxyalkyl, thioalkoxyalkyl, ((alkoxy)alkoxy)alkyl, arylalkyl or (heterocyclic)alkyl; and $R_4$ is loweralkyl, cycloalkylalkyl or arylalkyl; or a pharmaceutically acceptable salt, ester or prodrug thereof.

2. The compound of claim 1 wherein B is —NH—or —CH$_2$—; $R_1$ is arylalkyl; $R_3$ is (heterocyclic)alkyl; and $R_4$ is cycloalkylalkyl.

3. The compound of claim 2 wherein $R_1$ is benzyl and $R_4$ is cyclohexylmethyl.

4. A compound of the formula

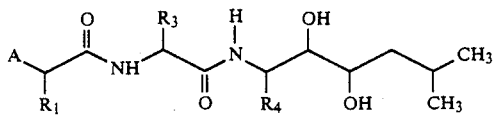

wherein

A is R₁₃—Q—CH₂— wherein

R₁₃ is ((heterocyclic)alkyl)(alkyl)amino and
Q is
(1) —C(O)— or
(2) —S(O)₂—,

R₁ is arylalkyl,

R₃ is (heterocyclic)alkyl and

R₄ is cyclohexylmethyl;

or a pharmaceutically acceptable salt, ester or prodrug thereof.

5. A compound selected from the group consisting of:
(2R)-2-Benzyl-3-((2-pyridin-2-ylethyl)(methyl)aminocarbonyl)propionyl-L-(1-pyrazolyl)Ala Amide of (2S,3R,4S)-2-Amino-1-cyclohexyl-3,4-dihydroxy-6-methylheptane;

(2R)-2-Benzyl-3-((2-pyridin-2-ylethyl)(methyl)aminocarbonyl)propionyl-L-(4-thiazolyl)Ala Amide of (2S,3R,4S)-2-Amino-1-cyclohexyl-3,4-dihydroxy-6-methylheptane;

(2R)-2-Benzyl-3-((2-morpholin-4-ylethyl)(methyl)aminocarbonyl)propionyl-L-(1-pyrazolyl)Ala Amide of (2S,3R,4S)-2-Amino-1-cyclohexyl-3,4-dihydroxy-6-methylheptane; or a pharmaceutically acceptable salt, ester or prodrug thereof.

6. A method for inhibiting renin comprising administering to a human in need of such treatment a therapeutically effective amount of a compound of claim 4.

7. A method for treating hypertension or congestive heart failure comprising administering to a mammal in need of such treatment a therapeutically effective amount of a compound of claim 4 alone or in combination with another antihypertensive agent.

8. A pharmaceutical composition for inhibiting renin comprising a pharmaceutical carrier and a therapeutically effective amount of a compound of claim 4.

9. A pharmaceutical composition for treating hypertension or congestive heart failure comprising a pharmaceutical carrier and a therapeutically effective amount of a compound of claim 4 alone in a combination with another antihypertensive agent.

10. (2R)-2-Benzyl-3-(1-methylazetidin-3-ylsulfonyl)propionyl-L-(4-thiazolyl)Ala Amide of (2S,3R,4S)-2-Amino-1-cyclohexyl-3,4-dihydroxy-6-methylheptane;

or a pharmaceutically acceptable salt, ester or prodrug thereof.

* * * * *